US008790879B2

(12) United States Patent
Getman et al.

(10) Patent No.: US 8,790,879 B2
(45) Date of Patent: Jul. 29, 2014

(54) **PROBES FOR DETECTING THE PRESENCE OF *TRICHOMONAS VAGINALIS* IN A SAMPLE**

(75) Inventors: Damon Kittredge Getman, Poway, CA (US); Barbara Susan Weinbaum, La Jolla, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

(21) Appl. No.: 13/011,811

(22) Filed: Jan. 21, 2011

(65) Prior Publication Data

US 2011/0183339 A1   Jul. 28, 2011

Related U.S. Application Data

(60) Provisional application No. 61/297,367, filed on Jan. 22, 2010.

(51) Int. Cl.
*C07H 21/02* (2006.01)
*C07H 21/04* (2006.01)
*C12Q 1/68* (2006.01)

(52) U.S. Cl.
CPC .............. *C12Q 1/6893* (2013.01); *C12Q 1/689* (2013.01); *C12Q 2600/156* (2013.01)
USPC ......... 435/6.15; 435/6.1; 435/6.11; 435/91.2; 536/24.32; 536/24.33

(58) Field of Classification Search
None
See application file for complete search history.

(56) References Cited

U.S. PATENT DOCUMENTS

| | | |
|---|---|---|
| 5,030,557 A | 7/1991 | Hogan et al. |
| 5,185,439 A | 2/1993 | Arnold, Jr. et al. |
| 5,288,611 A | 2/1994 | Kohne |
| 5,399,491 A | 3/1995 | Kacian et al. |
| 5,654,418 A | 8/1997 | Sheiness et al. |
| 5,985,563 A | 11/1999 | Hyldig-Nielsen et al. |
| 6,130,038 A | 10/2000 | Becker et al. |
| 6,150,517 A | 11/2000 | Hogan et al. |
| 6,361,945 B1 | 3/2002 | Becker et al. |
| 7,381,811 B2 | 6/2008 | Weisburg et al. |
| 7,632,934 B2 | 12/2009 | Weisburg et al. |
| 2004/0235138 A1* | 11/2004 | Weisburg et al. .......... 435/252.3 |
| 2005/0119211 A1* | 6/2005 | Chowrira et al. ............... 514/44 |
| 2008/0234473 A1 | 9/2008 | Weisburg et al. |
| 2008/0241893 A1 | 10/2008 | Weisburg et al. |

FOREIGN PATENT DOCUMENTS

WO        8904876 A1    6/1989

OTHER PUBLICATIONS

Brown et al., "Evaluation of the Affirm Ambient Temperature Transport System for the Detection and Identification of *Trichomonas vaginalis*, *Gardnerella vaginalis*, and *Candida* Species from Vaginal Fluid Specimens," J. Clin. MicrobioL, Sep. 2001, 39(9):3197-3199, ASM, USA.
Cotch et al., "*Trichomonas vaginalis* Associated With Low Birth Weight and Preterm Delivery," Sex. Transm. Dis., Jul. 1997, 24(6):353-360, Lippincott, USA.
Cu-Uvin et al., "Prevalence, Incidence, and Persistence or Recurrence of Trichomoniasis among Human Immunodeficiency Virus (HIV)-Positive Women and among HIV-Negative Women at High Risk for HIV Infection," Clin. Infect. Dis., May 2002, 34:1406-1411, The University of Chicago Press, USA.
Garcia, "Protozoa from Other Body Sites," Diagnostic Medical Parasitology, 2001, 4th ed., pp. 120-131, ASM Press, USA.
Gen-Bank Accession No. U17510, "*Trichomonas vaginalis* 16S-like rRNA gene," Nov. 30, 1995.
Gunderson et al., "Phylogeny of Trichomonads Inferred from Small-Subunit rRNA Sequences," J. Euk. MicrobioL, Jul.-Aug. 1995, 42(4):411-415, Society of Protozoologists. USA.
Jordan et al., "TaqMan-Based Detection of *Trichomonas vaginalis* DNA from Female Genital Specimens," J. Clin. MicrobioL, Nov. 2001, 39(11):3819-3822, ASM, USA.
Kaydos et al., "Development and Validation of a PCR-Based Enzyme-Linked Immunosorbent Assay with Urine for Use in Clinical Research Settings to Detect *Trichomonas vaginalis* in Women," J. Clin. MicrobioL, Jan. 2002, 40 (1):89-95, ASM, USA.
Kikuta et al., "Specific and sensitive detection of Trichomonas tenax by the polymerase chain reaction," Lett. AppL MicrobioL, 1997, 24:193-197, The Society for Applied Bacteriology, Blackwell Publishing, UK.
Krieger et al., "Diagnosis of Trichomoniasis—Comparison of Conventional Wet-Mount Examination With Cytologic Studies, Cultures, and Monoclonal Antibody Staining of Direct Specimens," JAMA, Feb. 1988, 259(8):1223-1227, American Medical Association, USA.
Leber et al., "Intestinal and Urogenital Amebae, Flagellates, and Ciliates," Manual of Clinical Microbiology, 7th ed., 1999, pp. 1391-1405, ASM Press, USA.
Mayata et al., "18S Ribosomal DNA-Based PCR for Diagnosis of *Trichomonas vaginalis*," J. Clin. Microbiol., Jul. 2000,38(7):2683-2687, ASM, USA.
Niccolai et al., "Incidence and Predictors of Reinfection with *Trichomonas vaginalis* in HIV-infected Women," Sex. Transm. Dis., May 2000,27(5):284-288, Lippincott, USA.
Rein, "*Trichomonas vaginalis*", Principles and Practice of Infectious Diseases, 5th ed., 2000, pp. 2894-2898, Churchill Livingstone, USA.
Sorvillo et al., "*Trichomonas vaginalis*, HIV, and African-Americans," Emerg. Infect. Dis., Nov.-Dec. 2001, 7 (6):927-932, CDC, USA.
Sorvillo et al., "Risk Factors for Trichomoniasis Among Women With Human Immunodeficiency Virus (HIV) Infection at a Public Clinic in Los Angeles County, California: Implications for HIV Prevention," Am. J. Trop. Med. Hyg., 1998, 58(4):495-500, The American Society of Tropical Medicine and Hygiene, USA.
Ter Kuile et al., "Influence of growth conditions on RNA levels in relation to activity of core metabolic enzymes in the parasitic protests *Trypanosoma brucei* and *Trichomonas vaginalis*," Microbiol., 1999, 145:755-765, SGM, UK.
Van Der Schee et al., "Improved Diagnosis of *Trichomonas vaginalis* Infection by PCR Using Vaginal Swabs and Urine Specimens Compared to Diagnosis by Wet Mount Microscopy, Culture, and Fluorescent Staining," J. Clin. Microbiol., Dec. 1999, 37(12):4127-4130, ASM, USA.

(Continued)

Primary Examiner — Carla Myers
(74) Attorney, Agent, or Firm — Charles B. Cappellari; Kathryn K. Hull

(57) ABSTRACT

Oligonucleotides useful for determining the presence of *Trichomonas vaginalis* in a test sample.

20 Claims, No Drawings

(56) References Cited

OTHER PUBLICATIONS

Wendel et al., "*Trichomonas vaginalis* Polymerase Chain Reaction Compared with Standard Diagnostic and Therapeutic Protocols for Detection and Treatment of *Vaginal Trichomoniasis*," Clin. Infect. Dis., Sep. 2002, 35:576-580, The University of Chicago Press, USA.

PCT Search Report, PCT/US11/22164, Jun. 8, 2011.

PCT Written Opinion, PCT/US11/22164, Jun. 8, 2011.

Adu-Sarkodie et al., "Lack of evidence for the involvement of rectal and oral trichomonads in the aetiology of vaginal trichomoniasis in Ghana," Sex. Transm. Infect. Jun. 21, 2006, 83(2):130-132, BMJ Publishing Group, United Kingdom.

Blaha et al., "In vitro activity of hexadecylphosphocholine (miltefosine) against metronidazole-resistant and -susceptible strains of *Trichomonas vaginalis*," J. Antimicrob. Chemother., Dec. 12, 2005, 57(2): 273-278, Oxford University Press, United Kingdom.

GenBank accession No. AY338473, "*Trichomonas vaginalis* strain ATCC 50138 small subunit ribosomal RNA gene, partial sequence," Jan. 27, 2006.

GenBank accession No. AY338474, "*Trichomonas vaginalis* strain ATCC 30236 small subunit ribosomal RNA gene, partial sequence," Jan. 27, 2006.

GenBank accession No. AY338475, "*Trichomonas vaginalis* strain ND MR 100 small subunit ribosomal RNA gene, partial sequence," Jan. 27, 2006.

GenBank accession No. AY338476, "*Trichomonas vaginalis* strain TV2 small subunit ribosomal RNA gene, partial sequence," Jan. 27, 2006.

CIPO Office Action, Canadian Patent Application No. 2,787,327, Oct. 9, 2012.

PCT International Preliminary Report on Patentability, International Application No. PCT/US11/22164, Aug. 2, 2012.

Caliendo et al., "Real-Time PCR improves detection of *Trichomonas vaginalis* infection compared with culture using self-collected vaginal swabs," Infect. Dis. Obs. Gyn., 2005, 13(3):145-150, Taylor & Francis, Oxford UK.

Mostegl et al., "Design and Successful Application of an Oligonucleotide Probe for Detection of Parasites of the Order Trichomonadida by Chromogenic In-Situ Hybridization," J. Comp. Pathol., 2009, 141(4):300, Academic Press, London UK. [Abstract Only].

Mostegl et al., "Design and validation of an oligonucleotide probe for the detection of protozoa from the order Trichomonadida using chromogenic in situ hybridization," Vet. Parasitol., 2010, 171:1-6, Elsevier B.V., Amsterdam, NL.

Simpson et al., "Real-time PCRs for detection of *Trichomonas vaginalis* β-tubulin and 18S rRNA genes in female genital specimens," J. Med. Microbiol., 2007, 56(6):772-777, SGM Journals, UK.

EPO, Extended European Search Report, European Patent Application No. 11735282.3, Aug. 21, 2013.

APO Patent Examination Report, Australian Patent Application No. 2012232987, Jun. 28, 2013.

EPO Patent Examination Report, European Patent Application No. 11735282.3, Mar. 17, 2014.

\* cited by examiner

SEQUENCE LISTING

```
<160> NUMBER OF SEQ ID NOS: 106

<210> SEQ ID NO 1
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 1
ttgccgaagt ccttcggtta aagttctaat tg                                  32

<210> SEQ ID NO 2
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 2
uugccgaagu ccuucgguua aaguucuaau ug                                  32

<210> SEQ ID NO 3
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 3
caattagaac tttaaccgaa ggacttcggc aa                                  32

<210> SEQ ID NO 4
<211> LENGTH: 32
<212> TYPE: RNA
<213> ORGANISM: Artificial Sequence
```

```
<220> FEATURE:
<223> OTHER INFORMATION: Synthetic Oligonucleotide

<400> SEQUENCE: 4
caauuagaac uuuaaccgaa ggacuucggc aa                                    32

<210> SEQ ID NO 5
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 5
tgccgaagtc cttcggttaa agttctaatt gg                                    32

<210> SEQ ID NO 6
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 6
ugccgaaguc cuucgguuaa aguucuaauu gg                                    32

<210> SEQ ID NO 7
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 7
ccaattagaa ctttaaccga aggacttcgg ca                                    32

<210> SEQ ID NO 8
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 8
ccaauuagaa cuuuaaccga aggacuucgg ca                                    32

<210> SEQ ID NO 9
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 9
gccgaagtcc ttcggttaaa gttctaattg g                                     32

<210> SEQ ID NO 10
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 10
gccgaagucc uucgguuaaa guucuaauug g                                     32
```

```
<210> SEQ ID NO 11
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 11
cccaattaga actttaaccg aaggacttcg gc                                  32

<210> SEQ ID NO 12
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 12
cccaauuaga acuuuaaccg aaggacuucg gc                                  32

<210> SEQ ID NO 13
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 13
ccgaagtcct tcggttaaag ttctaattgg g                                   31

<210> SEQ ID NO 14
<211> LENGTH: 31
<212> TYPE: RNA
<213> ORGANISM: Artificial Sequence
<220> FEATURE:
<223> OTHER INFORMATION: Synthetic Oligonucleotide

<400> SEQUENCE: 14
ccgaaguccu ucgguuaaag uucuaauugg g                                   31

<210> SEQ ID NO 15
<211> LENGTH: 31
<212> TYPE: DNA
<213> ORGANISM: Artificial Sequence
<220> FEATURE:
<223> OTHER INFORMATION: Synthetic Oligonucleotide

<400> SEQUENCE: 15
cccaattaga actttaaccg aaggacttcg g                                   31

<210> SEQ ID NO 16
<211> LENGTH: 31
<212> TYPE: RNA
<213> ORGANISM: Artificial Sequence
<220> FEATURE:
<223> OTHER INFORMATION: Synthetic Oligonucleotide

<400> SEQUENCE: 16
cccaauuaga acuuuaaccg aaggacuucg g                                   31

<210> SEQ ID NO 17
<211> LENGTH: 32
<212> TYPE: DNA
<213> ORGANISM: Artificial Sequence
<220> FEATURE:
<223> OTHER INFORMATION: Synthetic Oligonucleotide
```

```
<400> SEQUENCE: 17
cgaagtcctt cggttaaagt tctaattggg ac                                  32

<210> SEQ ID NO 18
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 18
cgaaguccuu cgguuaaagu ucuaauuggg ac                                  32

<210> SEQ ID NO 19
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 19
gtcccaatta gaactttaac cgaaggactt cg                                  32

<210> SEQ ID NO 20
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 20
gucccaauua gaacuuuaac cgaaggacuu cg                                  32

<210> SEQ ID NO 21
<211> LENGTH: 32
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: n
<222> LOCATION: (8)..(8)
<223> OTHER INFORMATION: "n" is inosine

<400> SEQUENCE: 21
cgaagtcntt cggttaaagt tctaattggg ac                                  32

<210> SEQ ID NO 22
<211> LENGTH: 32
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: n
<222> LOCATION: (8)..(8)
<223> OTHER INFORMATION: "n" is inosine

<400> SEQUENCE: 22
cgaagucnuu cgguuaaagu ucuaauuggg ac                                  32

<210> SEQ ID NO 23
<211> LENGTH: 32
<212> TYPE: DNA
<213> ORGANISM: Artificial Sequence
<220> FEATURE:
```

```
<223> OTHER INFORMATION: Synthetic Oligonucleotide
<220> FEATURE:
<221> NAME/KEY: n
<222> LOCATION: (25)..(25)
<223> OTHER INFORMATION: "n" is inosine

<400> SEQUENCE: 23
gtcccaatta gaactttaac cgaangactt cg                                32

<210> SEQ ID NO 24
<211> LENGTH: 32
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: n
<222> LOCATION: (25)..(25)
<223> OTHER INFORMATION: "n" is inosine

<400> SEQUENCE: 24
gucccaauua gaacuuuaac cgaangacuu cg                                32

<210> SEQ ID NO 25
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 25
gaagtccttc ggttaaagtt ctaa                                         24

<210> SEQ ID NO 26
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 26
gaaguccuuc gguuaaaguu cuaa                                         24

<210> SEQ ID NO 27
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 27
ttagaacttt aaccgaagga cttc                                         24

<210> SEQ ID NO 28
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 28
uuagaacuuu aaccgaagga cuuc                                         24

<210> SEQ ID NO 29
<211> LENGTH: 25
<212> TYPE: DNA
<213> ORGANISM: Artificial Sequence
```

```
<220> FEATURE:
<223> OTHER INFORMATION: Synthetic Oligonucleotide

<400> SEQUENCE: 29
gtccttcggt taaagttcta attgg                                              25

<210> SEQ ID NO 30
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 30
guccuucggu uaaaguucua auugg                                              25

<210> SEQ ID NO 31
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 31
ccaattagaa ctttaaccga aggac                                              25

<210> SEQ ID NO 32
<211> LENGTH: 25
<212> TYPE: RNA
<213> ORGANISM: Artificial Sequence
<220> FEATURE:
<223> OTHER INFORMATION: Synthetic Oligonucleotide

<400> SEQUENCE: 32
ccaauuagaa cuuuaaccga aggac                                              25

<210> SEQ ID NO 33
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 33
ttcggttaaa gttctaattg ggactccctg cg                                      32

<210> SEQ ID NO 34
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 34
uucgguuaaa guucuaauug ggacucccug cg                                      32

<210> SEQ ID NO 35
<211> LENGTH: 32
<212> TYPE: DNA
<213> ORGANISM: Artificial Sequence
<220> FEATURE:
<223> OTHER INFORMATION: Synthetic Oligonucleotide

<400> SEQUENCE: 35
cgcagggagt cccaattaga actttaaccg aa                                      32
```

```
<210> SEQ ID NO 36
<211> LENGTH: 32
<212> TYPE: RNA
<213> ORGANISM: Artificial Sequence
<220> FEATURE:
<223> OTHER INFORMATION: Synthetic Oligonucleotide

<400> SEQUENCE: 36
cgcagggagu cccaauuaga acuuuaaccg aa                                    32

<210> SEQ ID NO 37
<211> LENGTH: 44
<212> TYPE: DNA
<213> ORGANISM: Trichomonas vaginalis

<400> SEQUENCE: 37
ttgccgaagt ccttcggtta aagttctaat tgggactccc tgcg                       44

<210> SEQ ID NO 38
<211> LENGTH: 44
<212> TYPE: RNA
<213> ORGANISM: Trichomonas vaginalis

<400> SEQUENCE: 38
uugccgaagu ccuucgguua aaguucuaau ugggacuccc ugcg                       44

<210> SEQ ID NO 39
<211> LENGTH: 44
<212> TYPE: DNA
<213> ORGANISM: Trichomonas vaginalis

<400> SEQUENCE: 39
cgcagggagt cccaattaga actttaaccg aaggacttcg gcaa                       44

<210> SEQ ID NO 40
<211> LENGTH: 44
<212> TYPE: RNA
<213> ORGANISM: Trichomonas vaginalis

<400> SEQUENCE: 40
cgcagggagu cccaauuaga acuuuaaccg aaggacuucg gcaa                       44

<210> SEQ ID NO 41
<211> LENGTH: 17
<212> TYPE: DNA
<213> ORGANISM: Trichomonas vaginalis

<400> SEQUENCE: 41
ttcggttaaa gttctaa                                                     17

<210> SEQ ID NO 42
<211> LENGTH: 17
<212> TYPE: RNA
<213> ORGANISM: Trichomonas vaginalis

<400> SEQUENCE: 42
uucgguuaaa guucuaa                                                     17

<210> SEQ ID NO 43
<211> LENGTH: 17
<212> TYPE: DNA
<213> ORGANISM: Trichomonas vaginalis

<400> SEQUENCE: 43
```

```
ttagaactttaaccgaa                                                    17

<210> SEQ ID NO 44
<211> LENGTH: 17
<212> TYPE: RNA
<213> ORGANISM: Trichomonas vaginalis

<400> SEQUENCE: 44 uuagaacuuuaaccgaa                                                    17

<210> SEQ ID NO 45
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 45
gctaacgagc gagattatcg cc                                             22

<210> SEQ ID NO 46
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 46
gcuaacgagc gagauuaucg cc                                             22

<210> SEQ ID NO 47
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 47
ggcgataatc tcgctcgtta gc                                             22

<210> SEQ ID NO 48
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 48
ggcgauaauc ucgcucguua gc                                             22

<210> SEQ ID NO 49
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 49
ggcatcacgg acctgttatt gc                                             22

<210> SEQ ID NO 50
<211> LENGTH: 22
<212> TYPE: RNA
<213> ORGANISM: Artificial Sequence
<220> FEATURE:
```

<223> OTHER INFORMATION: Synthetic Oligonucleotide

<400> SEQUENCE: 50
ggcaucacgg accuguuauu gc                                           22

<210> SEQ ID NO 51
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 51
gcaataacag gtccgtgatg cc                                           22

<210> SEQ ID NO 52
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 52
gcaauaacag guccgugaug cc                                           22

<210> SEQ ID NO 53
<211> LENGTH: 49
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: Promoter Primer
<222> LOCATION: (1)..(27)
<223> OTHER INFORMATION: T7 RNA polymerse promoter sequence

<400> SEQUENCE: 53
aatttaatac gactcactat agggagaggc atcacggacc tgttattgc              49

<210> SEQ ID NO 54
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 54
aatttaatac gactcactat agggaga                                      27

<210> SEQ ID NO 55
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 55
gcctgctgct acccgtggat at                                           22

<210> SEQ ID NO 56
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 56
gccugcugcu acccguggau au                                           22

<210> SEQ ID NO 57
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 57
atatccacgg gtagcagcag gc                                           22

<210> SEQ ID NO 58
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 58
auauccacgg guagcagcag gc                                           22

<210> SEQ ID NO 59
<211> LENGTH: 55
<212> TYPE: DNA
<213> ORGANISM: Artificial Sequence
<220> FEATURE:
<223> OTHER INFORMATION: Synthetic Oligonucleotide

<400> SEQUENCE: 59
gcctgctgct acccgtggat attttaaaaa aaaaaaaaa aaaaaaaaaa aaaaa        55

<210> SEQ ID NO 60
<211> LENGTH: 34
<212> TYPE: DNA
<213> ORGANISM: Artificial Sequence
<220> FEATURE:
<223> OTHER INFORMATION: Synthetic Oligonucleotide

<400> SEQUENCE: 60
tttaaaaaaa aaaaaaaaaa aaaaaaaaaa aaaa                              34

<210> SEQ ID NO 61
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 61
gctaacgagc gagattatcg ccaagcaata acaggtccgt gatg                   44

<210> SEQ ID NO 62
<211> LENGTH: 36
<212> TYPE: DNA
<213> ORGANISM: Artificial Sequence
<220> FEATURE:
<223> OTHER INFORMATION: Synthetic Oligonucleotide

<400> SEQUENCE: 62
gtcccaatta gaactttaac cgaaggactt cggcaa                            36

<210> SEQ ID NO 63
<211> LENGTH: 32
<212> TYPE: DNA

```
<213> ORGANISM: Artificial Sequence
<220> FEATURE:
<223> OTHER INFORMATION: Synthetic Oligonucleotide

<400> SEQUENCE: 63
cgcagggagt cccaattaga actttaaccg aa                                32

<210> SEQ ID NO 64
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 64
caattagaac tttaaccgaa g                                            21

<210> SEQ ID NO 65
<211> LENGTH: 23
<212> TYPE: DNA
<213> ORGANISM: Artificial Sequence
<220> FEATURE:
<223> OTHER INFORMATION: Synthetic Oligonucleotide

<400> SEQUENCE: 65
ttgcttggcg ataatctcgc tcg                                          23

<210> SEQ ID NO 66
<211> LENGTH: 27
<212> TYPE: DNA
<213> ORGANISM: Artificial Sequence
<220> FEATURE:
<223> OTHER INFORMATION: Synthetic Oligonucleotide

<400> SEQUENCE: 66
cctgttattg cttggcgata atctcgc                                      27

<210> SEQ ID NO 67
<211> LENGTH: 29
<212> TYPE: DNA
<213> ORGANISM: Artificial Sequence
<220> FEATURE:
<223> OTHER INFORMATION: Synthetic Oligonucleotide

<400> SEQUENCE: 67
cggacctgtt attgcttggc gataatctc                                    29

<210> SEQ ID NO 68
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 68
gcctctcggc tttgcagtcc tatt                                         24

<210> SEQ ID NO 69
<211> LENGTH: 15
<212> TYPE: DNA
<213> ORGANISM: Artificial Sequence
<220> FEATURE:
<223> OTHER INFORMATION: Synthetic Oligonucleotide

<400> SEQUENCE: 69
gttgatcctg ccaag                                                   15
```

<210> SEQ ID NO 70
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 70
gccatgcaag tgttag                                                     16

<210> SEQ ID NO 71
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 71
ccattcgact gagtgaccta tc                                              22

<210> SEQ ID NO 72
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 72
gattcctggt tcatgacgct g                                               21

<210> SEQ ID NO 73
<211> LENGTH: 16
<212> TYPE: DNA
<213> ORGANISM: Artificial Sequence
<220> FEATURE:
<223> OTHER INFORMATION: Synthetic Oligonucleotide

<400> SEQUENCE: 73
ccgagtcatc caatcg                                                     16

<210> SEQ ID NO 74
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 74
cctaccgtta ccttgttacg ac                                              22

<210> SEQ ID NO 75
<211> LENGTH: 24
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: Methoxy
<222> LOCATION: (1)..(24)
<223> OTHER INFORMATION: 2'-O-Methyl RNA

<400> SEQUENCE: 75
gaaguccuuc gguuaaaguu cuaa                                            24

<210> SEQ ID NO 76

-continued

```
<211> LENGTH: 25
<212> TYPE: RNA
<213> ORGANISM: Artificial Sequence
<220> FEATURE:
<223> OTHER INFORMATION: Synthetic Oligonucleotide
<220> FEATURE:
<221> NAME/KEY: Methoxy
<222> LOCATION: (1)..(25)
<223> OTHER INFORMATION: 2'-O-Methyl RNA

<400> SEQUENCE: 76
guccuucggu uaaaguucua auugg                                         25

<210> SEQ ID NO 77
<211> LENGTH: 30
<212> TYPE: DNA
<213> ORGANISM: Trichomonas vaginalis

<400> SEQUENCE: 77
gtgcgtgggt tgacctgtct agcgttgatt                                    30

<210> SEQ ID NO 78
<211> LENGTH: 30
<212> TYPE: RNA
<213> ORGANISM: Trichomonas vaginalis

<400> SEQUENCE: 78
gugcgugggu ugaccugucu agcguugauu                                    30

<210> SEQ ID NO 79
<211> LENGTH: 30
<212> TYPE: DNA
<213> ORGANISM: Trichomonas vaginalis

<400> SEQUENCE: 79
aatcaacgct agacaggtca acccacgcac                                    30

<210> SEQ ID NO 80
<211> LENGTH: 30
<212> TYPE: RNA
<213> ORGANISM: Trichomonas vaginalis

<400> SEQUENCE: 80
aaucaacgcu agacagguca acccacgcac                                    30

<210> SEQ ID NO 81
<211> LENGTH: 10
<212> TYPE: DNA
<213> ORGANISM: Trichomonas vaginalis

<400> SEQUENCE: 81
gacctgtcta                                                          10

<210> SEQ ID NO 82
<211> LENGTH: 10
<212> TYPE: RNA
<213> ORGANISM: Trichomonas vaginalis

<400> SEQUENCE: 82
gaccugucua                                                          10

<210> SEQ ID NO 83
<211> LENGTH: 10
<212> TYPE: DNA
<213> ORGANISM: Trichomonas vaginalis
```

```
<400> SEQUENCE: 83
tagacaggtc                                                              10

<210> SEQ ID NO 84
<211> LENGTH: 10
<212> TYPE: RNA
<213> ORGANISM: Trichomonas vaginalis

<400> SEQUENCE: 84
uagacagguc                                                              10

<210> SEQ ID NO 85
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 85
ctagacaggt caacccacgc ac                                                22

<210> SEQ ID NO 86
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 86
cuagacaggu caacccacgc ac                                                22

<210> SEQ ID NO 87
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 87
gtgcgtgggt tgacctgtct ag                                                22

<210> SEQ ID NO 88
<211> LENGTH: 22
<212> TYPE: RNA
<213> ORGANISM: Artificial Sequence
<220> FEATURE:
<223> OTHER INFORMATION: Synthetic Oligonucleotide

<400> SEQUENCE: 88
gugcgugggu ugaccugucu ag                                                22

<210> SEQ ID NO 89
<211> LENGTH: 55
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: Methoxy
<222> LOCATION: (1)..(22)
<223> OTHER INFORMATION: 2'-O-Methyl RNA

<400> SEQUENCE: 89
cuagacaggu caacccacgc actttaaaaa aaaaaaaaaa aaaaaaaaaa aaaaa            55
```

<210> SEQ ID NO 90
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 90
aatcaacgct agacaggtca accc                                    24

<210> SEQ ID NO 91
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 91
aaucaacgcu agacagguca accc                                    24

<210> SEQ ID NO 92
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 92
gggttgacct gtctagcgtt gatt                                    24

<210> SEQ ID NO 93
<211> LENGTH: 24
<212> TYPE: RNA
<213> ORGANISM: Artificial Sequence
<220> FEATURE:
<223> OTHER INFORMATION: Synthetic Oligonucleotide

<400> SEQUENCE: 93
ggguugaccu gucuagcguu gauu                                    24

<210> SEQ ID NO 94
<211> LENGTH: 57
<212> TYPE: DNA
<213> ORGANISM: Artificial Sequence
<220> FEATURE:
<223> OTHER INFORMATION: Synthetic Oligonucleotide

<400> SEQUENCE: 94
aatcaacgct agacaggtca accctttaaa aaaaaaaaa aaaaaaaaaa aaaaaaa    57

<210> SEQ ID NO 95
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 95
tcaacgctag acaggtcaa                                          19

<210> SEQ ID NO 96
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 96
ucaacgcuag acaggucaa                                              19

<210> SEQ ID NO 97
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 97
ttgacctgtc tagcgttga                                              19

<210> SEQ ID NO 98
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 98
uugaccuguc uagcguuga                                              19

<210> SEQ ID NO 99
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 99
tcaacgctag acaggtcaat ttaaaaaaaa aaaaaaaaaa aaaaaaaaaa aa          52

<210> SEQ ID NO 100
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 100
aatcaacgct agacaggtc                                              19

<210> SEQ ID NO 101
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 101
aaucaacgcu agacagguc                                              19

<210> SEQ ID NO 102
<211> LENGTH: 19
<212> TYPE: DNA
<213> ORGANISM: Artificial Sequence
<220> FEATURE:
<223> OTHER INFORMATION: Synthetic Oligonucleotide

<400> SEQUENCE: 102
gacctgtcta gcgttgatt                                              19

<210> SEQ ID NO 103

```
<211> LENGTH: 19
<212> TYPE: RNA
<213> ORGANISM: Artificial Sequence
<220> FEATURE:
<223> OTHER INFORMATION: Synthetic Oligonucleotide

<400> SEQUENCE: 103
gaccugucua gcguugauu                                                       19

<210> SEQ ID NO 104
<211> LENGTH: 52
<212> TYPE: DNA
<213> ORGANISM: Artificial Sequence
<220> FEATURE:
<223> OTHER INFORMATION: Synthetic Oligonucleotide

<400> SEQUENCE: 104
aatcaacgct agacaggtct ttaaaaaaaa aaaaaaaaaa aaaaaaaaaa aa                  52

<210> SEQ ID NO 105
<211> LENGTH: 57
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: Methoxy
<222> LOCATION: (1)..(24)
<223> OTHER INFORMATION: 2'-O-Methyl RNA

<400> SEQUENCE: 105
aaucaacgcu agacagguca accctttaaa aaaaaaaaaa aaaaaaaaaa aaaaaaa             57

<210> SEQ ID NO 106
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: Methoxy
<222> LOCATION: (1)..(19)
<223> OTHER INFORMATION: 2'-O-Methyl RNA

<400> SEQUENCE: 106
ucaacgcuag acaggucaat ttaaaaaaaa aaaaaaaaaa aaaaaaaaaa aa                  52
```

PROBES FOR DETECTING THE PRESENCE OF *TRICHOMONAS VAGINALIS* IN A SAMPLE

FIELD OF THE INVENTION

The present disclosure relates to detection probes, capture probes, amplification oligonucleotides, nucleic acid compositions, probe mixes, methods, and kits useful for determining the presence of *Trichomonas vaginalis* in a test sample.

BACKGROUND OF THE INVENTION

*Trichomonas vaginalis* is protozoan parasite that causes trichomoniasis, one of the most common and treatable of the sexually transmitted diseases. *Trichomonas vaginalis* is a relatively delicate pear-shaped trophozoite that is typically 7 to 23 µm long by 5 to 12 µm wide. The organism has four anterior flagella and a fifth forming the outer edge of a short undulating membrane. The anterior flagella propels the organism through liquid in a jerky, rapid fashion, sometimes causing the organism to rotate as it moves. *Trichomonas vaginalis* divides by binary fission in the urogenital tract of those infected. The organism is translucent and colorless, or slightly grey in appearance under the microscope. A slender rod, the axostyle, extends the length of the body and protrudes posteriorly. The nucleus is near-anterior and appears well-defined, containing many chromatin granules. The appearance of *T. vaginalis* is very similar to that of other trichomonads, such as *Trichomonas tenax*, although only *T. vaginalis* is found in genitourinary tract infections.

Worldwide, *T. vaginalis* infects approximately 180 million people per year, usually by direct person-to-person contact, making it the most common sexually transmitted disease (STD) agent. In the United States, it is believed that *T. vaginalis* infects an estimated 7 million people annually. Despite its prevalence and geographic distribution, *T. vaginalis* has not been the focus of intensive study. Indeed, it is not even listed as a "reportable disease" by the U.S. Centers for Disease Control, and there are no active control or prevention programs. Recent reports, however, suggest growing public health interest in this pathogen. Infections in women are known to cause vaginitis, urethritis, and cervicitis. Severe infections are accompanied by a foamy, yellowish-green discharge with a foul odor, and small hemorrhagic lesions may also be present in the genitourinary tract. Complications include premature labor, low-birth weight offspring, premature rupture of membranes, and post-abortion and post-hysterectomy infection. An association with pelvic inflammatory disease, tubal infertility, and cervical cancer have been reported. *Trichomonas vaginalis* has also been implicated as a co-factor in the transmission of HIV and other STD agents. The organism can also be passed to neonates during passage through the birth canal.

In men, symptoms of trichomoniasis include urethral discharge, urethral stricture, epididymitis, the urge to urinate, and a burning sensation with urination. In both men and women, infections with *T. vaginalis* are usually asymptomatic and may be self-limiting. It is estimated that, in women, 10-50% of *T. vaginalis* infections are asymptomatic, with the proportion in men probably being even higher. That said, with many women the infection becomes symptomatic and chronic, with periods of relief in response to therapy. Recurrence may be caused by re-infection from an asymptomatic sexual partner, or by failure of the standard course of therapy (a regimen of the antibiotic metronidazole). And while *T. vaginalis* infections almost always occur in the genitourinary tract, on rare occasions they occur at ecotopic sites, and the parasite may be recovered from other areas of a patient's body.

As a result of suboptimal comparative laboratory methods and a focus on other STD sources, studies of *T. vaginalis* have often substantially underestimated the prevalence of infection. Despite this, levels of infection typically have been high, with reported overall prevalence rates ranging from 3-58%, with an unweighted average across studies of 21% (Cu-Uvin et al. *Clin. Infect. Dis.* (2002) 34(10):1406-11). In studies that presented information on race/ethnicity, *T. vaginalis* infection rates have been reported to be highest among African-Americans (Sorvillo et al. *Emerg. Infect. Dis.* (2001) 7(6): 927-32). The following chart illustrates the trend reported by Sorvillo et al., with regard to the prevalence of infection in terms of the percentage of patients infected with trichomoniasis, chlamydia, and/or gonorrhea at certain health clinics in Baltimore, Md. (B) and in New York, N.Y. (NY).

| Year | Patient Number | City | Trichomoniasis (%) | Chlamydia (%) | Gonorrhea (%) |
|---|---|---|---|---|---|
| 1996 | 213 | NY | 51 | 9 | 5 |
| 1994 | 372 | NY | 27 | 7 | 2 |
| 1994 | 1404 | NY | 20 | 15 | No Data |
| 1992 | 279 | B | 26 | 21 | 14 |
| 1990-94 | 677 | NY | 22 | 6 | 1 |

Following exposure, the incubation period ranges from about 5 to 10 days, although periods as short as 1 day to as many as 28 days have been reported. If diagnosed, *T. vaginalis* infections can be readily treated by orally administered antibiotics.

Given its relative prevalence and association with other STDs, there is increasing interest in effectively diagnosing trichomoniasis. Conventional diagnostic methods for detecting *T. vaginalis*, however, are based on direct examination, "wet mount" microscopy, or cell culture, each of which has its own shortcomings. With regard to direct patient examination, other infections mimic the appearance and odor of the vaginal discharge. Accordingly, laboratory techniques such as microscopy, antibody detection, and cell culture are often used. While it is possible to detect *T. vaginalis* using a "wet mount" prepared by mixing vaginal secretions with saline on a slide and examining the slide under a microscope for the presence of organisms having the characteristic size, shape, and motility of *T. vaginalis*, the sensitivity of such methods depends highly on the skill and experience of the microscopist, as well as the time spent transporting specimen to a laboratory. Wet mount diagnosis has been found to be only 35-80% as sensitive as other methods, such as cell culture, in detecting the presence of *T. vaginalis*. Other direct methods, such as fluorescent antibody detection and enzyme-linked immunoassays, have also been developed, as has a non-amplified, DNA probe-based method (Affirm, Becton Dickinson), although their sensitivities, as compared to cell culture, range from 70-90%. For these reasons, cell culture is considered the current "gold standard" for clinical detection of *T. vaginalis*. Due to its relatively delicate nature, however, culturing the organism is technically challenging, and typically requires up to 7 days for maximum sensitivity. Even then, the sensitivity of cell culture methods is estimated to be only about 85-95% due to problems associated with time lapses between sample recovery and culture inoculation, maintaining proper incubation conditions, visualizing low numbers of the organism and/or the motility of the protozoa.

Given the human health implications of trichomoniasis and relative inability of existing clinical laboratory methods to selectively and sensitively detect *T. vaginalis* from a test sample, a need clearly exists for a sensitive and specific assay which can be used to determine the presence of *T. vaginalis* in a particular sample of biological material.

SUMMARY OF THE INVENTION

The present disclosure provides a solution to the clinical need for a sensitive assay specific for *T. vaginalis* by featuring oligonucleotides that are useful for determining whether *T. vaginalis* is present in a test sample, such as a genitourinary specimen.

Detection probes are provided that preferentially hybridize to a target region present in nucleic acid derived from *T. vaginalis* to form a detectable probe:target hybrid indicating the presence of *T. vaginalis*. In one embodiment, the disclosure provides detection probes for determining whether *T. vaginalis* is present in a test sample derived from a biological material obtained from, for example, the genitourinary tract of a patient. The detection probes contain a target-complementary base sequence that is perfectly complementary to a target sequence contained within a target domain derived from *T. vaginalis*, where the target domain is selected from the group consisting of (reading 5' to 3'):

SEQ ID NO: 37
ttgccgaagtccttcggttaaagttctaattgggactccctgcg,

SEQ ID NO: 38
uugccgaaguccuucgguuaaaguucuaauugggacucccugcg,

SEQ ID NO: 39
cgcagggagtcccaattagaactttaaccgaaggacttcggcaa,

SEQ ID NO: 40
cgcagggagucccaauuagaacuuuaaccgaaggacuucggcaa, and RNA/DNA combination equivalents of the foregoing. The target-complementary base sequence of the detection probes includes the base sequence of (reading 5' to 3'):

| SEQ ID NO: 41 | ttcggttaaagttctaa, |
| SEQ ID NO: 42 | uucgguuaaaguucuaa, |
| SEQ ID NO: 43 | ttagaactttaaccgaa, |
| SEQ ID NO: 44 | uuagaacuuuaaccgaa, | and RNA/DNA combination equivalents of the foregoing.

In one embodiment, the detection probes contain a target-complementary base sequence having a base sequence selected from the group consisting of (reading 5' to 3'):

| SEQ ID NO: 1 | ttgccgaagtccttcggttaaagttctaattg, |
| SEQ ID NO: 2 | uugccgaaguccuucgguuaaaguucuaauug, |
| SEQ ID NO: 3 | caattagaactttaaccgaaggacttcggcaa, |
| SEQ ID NO: 4 | caauuagaacuuuaaccgaaggacuucggcaa, |
| SEQ ID NO: 5 | tgccgaagtccttcggttaaagttctaattgg, |
| SEQ ID NO: 6 | ugccgaaguccuucgguuaaaguucuaauugg, |
| SEQ ID NO: 7 | ccaattagaactttaaccgaaggacttcggca, |
| SEQ ID NO: 8 | ccaauuagaacuuuaaccgaaggacuucggca, |
| SEQ ID NO: 9 | gccgaagtccttcggttaaagttctaattggg, |
| SEQ ID NO: 10 | gccgaaguccuucgguuaaaguucuaauuggg, |
| SEQ ID NO: 11 | cccaattagaactttaaccgaaggacttcggc, |
| SEQ ID NO: 12 | cccaauuagaacuuuaaccgaaggacuucggc, |
| SEQ ID NO: 13 | ccgaagtccttcggttaaagttctaattggg, |
| SEQ ID NO: 14 | ccgaaguccuucgguuaaaguucuaauuggg, |
| SEQ ID NO: 15 | cccaattagaactttaaccgaaggacttcgg, |
| SEQ ID NO: 16 | cccaauuagaacuuuaaccgaaggacuucgg, |
| SEQ ID NO: 17 | cgaagtccttcggttaaagttctaattgggac, |
| SEQ ID NO: 18 | cgaaguccuucgguuaaaguucuaauugggac, |
| SEQ ID NO: 19 | gtcccaattagaactttaaccgaaggacttcg, |
| SEQ ID NO: 20 | gucccaauuagaacuuuaaccgaaggacuucg, |
| SEQ ID NO: 21 | cgaagtcittcggttaaagttctaattgggac, |
| SEQ ID NO: 22 | cgaaguciuucgguuaaaguucuaauugggac, |
| SEQ ID NO: 23 | gtcccaattagaactttaaccgaaigacttcg, |
| SEQ ID NO: 24 | gucccaauuagaacuuuaaccgaaigacuucg, |
| SEQ ID NO: 25 | gaagtccttcggttaaagttctaa, |
| SEQ ID NO: 26 | gaaguccuucgguuaaaguucuaa, |
| SEQ ID NO: 27 | ttagaactttaaccgaaggacttc, |
| SEQ ID NO: 28 | uuagaacuuuaaccgaaggacuuc, |
| SEQ ID NO: 29 | gtccttcggttaaagttctaattgg, |
| SEQ ID NO: 30 | guccuucgguuaaaguucuaauugg, |
| SEQ ID NO: 31 | ccaattagaactttaaccgaaggac, |
| SEQ ID NO: 32 | ccaauuagaacuuuaaccgaaggac, |
| SEQ ID NO: 33 | ttcggttaaagttctaattgggactccctgcg, |
| SEQ ID NO: 34 | uucgguuaaaguucuaauugggacucccugcg, |
| SEQ ID NO: 35 | cgcagggagtcccaattagaactttaaccgaa, |
| SEQ ID NO: 36 | cgcagggagucccaauuagaacuuuaaccgaa, | and RNA/DNA combination equivalents of the foregoing.

In the present disclosure, the detection probes may have a target-complementary base sequence of any length suitable to achieve the desired selectivity and specificity for *T. vaginalis*-derived nucleic acid. Detection probes of the present disclosure comprise an oligonucleotide up to 100 bases in length in one embodiment, or are from 25 to 50 bases in length in another embodiment, or are from 25 to 35 bases in length in yet another embodiment. In one embodiment, the target-complementary base sequence of the detection probes is perfectly complementary to the target sequence.

In one embodiment, the base sequence of the detection probe consists of a target-complementary base sequence contained within and comprising at least 25 contiguous bases of SEQ ID NO:33, SEQ ID NO:34, SEQ ID NO:35, SEQ ID NO:36, or an RNA/DNA combination equivalent of any of the foregoing, and, optionally, one or more base sequences that are non-complementary to a nucleic acid derived from *T. vaginalis*. An additional base sequence may be comprised of any desired base sequence, so long as it does not stably bind to nucleic acid derived from the *T. vaginalis* under stringent hybridization conditions or prevent stable hybridization of the probe to the target nucleic acid. By way of example, additional bases may be included if the base sequence of the target-complementary base sequence is incorporated into a "molecular beacon" probe. Molecular beacons are disclosed by Tyagi et al., "Detectably Labeled Dual Conformation Oligonucleotide Probes, Assays and Kits," U.S. Pat. No. 5,925,517, (the contents of which are hereby included by reference herein), and include a target-complementary base sequence which is bounded by two base sequences having regions which are at least partially complementary to each other. A more detailed description of molecular beacons is provided infra in the section entitled "Hybridization Assay Probes to *T. vaginalis* Ribosomal Nucleic Acid." An additional base sequence may be joined directly to the target-complementary base sequence or, for example, by means of a non-nucleotide linker.

Detection probes according to the disclosure form a probe: target hybrid stable for detection with nucleic acid derived from *T. vaginalis* under stringent conditions and does not form a hybrid stable for detection with nucleic acid derived from *Trichomonas tenax* (ATCC® No. 30207) under stringent conditions.

The target-complementary base sequence may consist of deoxyribonucleic acid (DNA), ribonucleic acid (RNA), a combination of DNA and RNA, or it may be a nucleic acid analog (e.g., a peptide nucleic acid) or contain one or more modified nucleosides (e.g., a ribonucleoside having a 2'-O-methyl substitution to the ribofuranosyl moiety). The target-complementary base sequence may additionally include molecules that do not hydrogen bond to adenine, cytosine, guanine, thymine or uracil, provided such molecules do not interfere with the ability of the detection probe to selectively and specifically bind to nucleic acid derived from *T. vaginalis* in the test sample. Such molecules could include, by way of example, abasic nucleotides or universal base analogues, such as 5-nitroindole, provided such molecules do not significantly affect duplex stability. See, e.g., Guo et al., "Artificial Mismatch Hybridization," U.S. Pat. No. 5,780,233, the contents of which are incorporated by reference herein.

Detection probes of the present disclosure may include a detectable label. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule, a chromophore, a base sequence region that is unable to stably hybridize to the target nucleic acid under the stated conditions, and mixtures of these. In one particular embodiment, the label is an acridinium ester (AE), for example, 4-(2-succinimidyloxycarbonyl ethyl)-phenyl-10-methylacridinium-9-carboxylate fluorosulfonate (hereinafter referred to as "standard AE") or 9[[4-[3-[(2,5-dioxo-1-pyrrolidinyl)oxy]-3-oxopropyl]phenoxy]carbonyl]-2, s10-dimethyl-acridinium trifluoromethane sulfonate (hereinafter referred to as "glower AE"). Detection probes of the present disclosure may also include groups of interacting labels. Such groups of interacting labels include, by way of example, the following groups: enzyme/substrate, enzyme/cofactor, luminescent/quencher, luminescent/adduct, dye dimers and Förrester energy transfer pairs.

In one embodiment of the present disclosure, a capture probe is provided for extracting a *T. vaginalis*-derived target nucleic acid present in a test sample. The base sequence of the capture probe consists of a target-complementary base sequence that is perfectly complementary to a target sequence contained within a target domain selected from the group consisting of (reading 5' to 3'):

SEQ ID NO: 77   gtgcgtgggttgacctgtctagcgttgatt,

SEQ ID NO: 78   gugcguggguugaccugucuagcguugauu,

SEQ ID NO: 79   aatcaacgctagacaggtcaacccacgcac,

SEQ ID NO: 80   aaucaacgcuagacaggucaacccacgcac, and RNA/DNA combination equivalents of the foregoing, and, optionally, at least one base sequence that is non-complementary to the *T. vaginalis*-derived target nucleic acid. The target-complementary base sequence of the capture probe includes the base sequence of (reading 5' to 3'):

SEQ ID NO: 81       gacctgtcta,

SEQ ID NO: 82       gaccugucua,

SEQ ID NO: 83       tagacaggtc,

SEQ ID NO: 84       uagacagguc, or an RNA/DNA combination equivalent of any of the foregoing.

In another embodiment, the target-complementary base sequence of the capture probe includes a base sequence selected from the group consisting of (reading 5' to 3'):

SEQ ID NO: 55       gcctgctgctacccgtggatat

SEQ ID NO: 56       gccugcugcuacccguggauau

SEQ ID NO: 57       atatccacgggtagcagcaggc

SEQ ID NO: 58       auauccacggguagcagcaggc

SEQ ID NO: 85       ctagacaggtcaacccacgcac,

SEQ ID NO: 86       cuagacaggucaacccacgcac,

SEQ ID NO: 87       gtgcgtgggttgacctgtctag,

SEQ ID NO: 88       gugcguggguugaccugucuag,

SEQ ID NO: 90       aatcaacgctagacaggtcaaccc,

SEQ ID NO: 91       aaucaacgcuagacaggucaaccc,

SEQ ID NO: 92       gggttgacctgtctagcgttgatt,

SEQ ID NO: 93       ggguugaccugucuagcguugauu,

SEQ ID NO: 95       tcaacgctagacaggtcaa,

SEQ ID NO: 96       ucaacgcuagacaggucaa,

SEQ ID NO: 97       ttgacctgtctagcgttga,

SEQ ID NO: 98       uugaccugucuagcguuga,

SEQ ID NO: 100      aatcaacgctagacaggtc,

SEQ ID NO: 101      aaucaacgcuagacagguc,

SEQ ID NO: 102      gacctgtctagcgttgatt,

SEQ ID NO: 103      gaccugucuagcguugauu, and RNA/DNA combination equivalents of the foregoing.

Capture probes according to the present disclosure may be immobilized on a solid support by means of ligand-ligate binding pairs, such as avidin-biotin linkages, but may also include an immobilized probe binding region. The immobilized probe binding region of the capture probes is comprised of any base sequence capable of stably hybridizing under assay conditions to an oligonucleotide that is bound to a solid support present in a test sample. In one embodiment, the immobilized probe binding region, is a poly dA, homopolymer tail positioned at the 3' end of the capture probe. In this embodiment, oligonucleotides bound to the solid support would include 5' poly dT tails of sufficient length to stably bind to the poly dA tails of the capture probes under assay conditions. In another embodiment, the immobilized probe binding region includes a poly dA tail which is about 30 adenines in length, and the capture probe includes a spacer region which is about 3 thymines in length for joining together the target-complementary base sequence and the immobilized probe binding region (SEQ ID NO: 50 tttaaaaaaaaaaaaaaaaaaaaaaaaaaaaaaa).

The present disclosure also features amplification oligonucleotides useful for determining the presence of *T. vaginalis* in an amplification assay. In one embodiment, the disclosure provides at least one amplification oligonucleotide for amplifying nucleic acid derived from *T. vaginalis* present in a test sample, where the base sequence of the amplification oligonucleotide consists of a 3' target-complementary base sequence up to 40 bases in length and containing the base sequence of:

```
SEQ ID NO: 45     gctaacgagcgagattatcgcc,

SEQ ID NO: 46     gcuaacgagcgagauuaucgcc,

SEQ ID NO: 47     ggcgataatctcgctcgttagc,

SEQ ID NO: 48     ggcgauaaucucgcucguuagc,

SEQ ID NO: 49     ggcatcacggacctgttattgc,

SEQ ID NO: 50     ggcaucacggaccuguuauugc,

SEQ ID NO: 51     gcaataacaggtccgtgatgcc,

SEQ ID NO: 52     gcaauaacagguccgugaugcc,
``` or an RNA/DNA combination equivalent of any of the foregoing and, optionally, includes a sequence located 5' to the 3' target-complementary base sequence that is non-complementary to a *T. vaginalis* derived nucleic acid. The optional sequence may be, for example, a sequence recognized by an RNA polymerase or which enhances initiation or elongation by RNA polymerase, such as the T7 promoter sequence of SEQ ID NO:54: aatttaatacgactcactatagggaga.

In another embodiment, the amplification oligonucleotides are employed in sets of at least two amplification oligonucleotides. In one set, a first amplification oligonucleotide is included, the base sequence of which consists of a 3' target-complementary base sequence up to 40 bases in length and containing the base sequence of SEQ ID NO:45, SEQ ID NO:46, SEQ ID NO:47, SEQ ID NO:48, or an RNA/DNA combination equivalent of any of the foregoing and, optionally, a 5' sequence that is non-complementary to a *T. vaginalis* derived nucleic acid. The base sequence of a second amplification oligonucleotide of the set consists of a 3' target-complementary base sequence up to 40 bases in length and containing the base sequence of SEQ ID NO:49, SEQ ID NO:50, SEQ ID NO:51, SEQ ID NO:52, or an RNA/DNA combination equivalent of any of the foregoing and, optionally, a 5' sequence that is non-complementary to a *T. vaginalis* derived nucleic acid. The optional sequence may be, for example, a sequence recognized by an RNA polymerase or which enhances initiation or elongation by RNA polymerase, such as the T7 promoter sequence of SEQ ID NO:54.

The present disclosure, also a relates to probe mixes for determining the presence of *T. vaginalis* in a test sample. In one embodiment, the probe mix includes at least one of the above-described detection probes and at least one of the above-described capture probes. In another embodiment, the probe mix includes at least one of the above-described detection probes and at least one of the above-described amplification oligonucleotides. In another embodiment, the probe mix includes at least one of the above-described detection probes, at least one of the above-described capture probes, and at least one of the above-described amplification oligonucleotides. In another embodiment, the probe mix includes at least one of the above-described detection probes, at least one of the above-described capture probes, and at least two of the above-described amplification oligonucleotides. In another embodiment, the probe mix includes at least one of the above-described detection probes and at least two of the above-described capture probes. In another embodiment, the probe mix includes at least one of the above-described detection probes and at least two of the above-described amplification oligonucleotides. In another embodiment, the probe mix includes at least one of the above-described detection probes, at least two of the above-described capture probes, and at least one of the above-described amplification oligonucleotides. In another embodiment, the probe mix includes at least one of the above-described detection probes, at least two of the above-described capture probes, and at least two of the above described amplification oligonucleotides.

The present disclosure further features methods for determining whether *T. vaginalis* is present in a test sample. In one embodiment, the method comprises the steps of contacting the test sample with at least one of the above-described detection probes for detecting *T. vaginalis* under stringent conditions, and determining whether the probe:target hybrid has formed as an indication of the presence or absence of *T. vaginalis* in the test sample. This method may further include the step of quantifying the amount of hybrid present in the test sample as a means for estimating the amount of *T. vaginalis* present in the test sample. In another embodiment, the method comprises contacting the test sample with at least one of the above-described detection probes and at least one of the above-described capture probes under stringent conditions. In another embodiment, the method comprises contacting the test sample with at least one of the above-described detection probes under stringent conditions, and at least one of the above described amplification oligonucleotides under amplification conditions. In another embodiment, the method comprises contacting the test sample with at least one of the above-described detection probes and at least one of the above described capture probes under stringent conditions, and at least one of the above-described amplification oligonucleotides under amplification conditions. In another embodiment, the method comprises contacting the test sample with at least one of the above-described detection probes and at least one of the above described capture probes under stringent conditions, and at least two of the above-described amplification oligonucleotides under amplification conditions. In another embodiment, the method comprises contacting the test sample with at least one of the above-described detection probes and at least two of the above-described capture probes under stringent conditions. In another embodiment, the method comprises contacting the test sample with at least one of the above-described detection probes under stringent conditions, and least two of the above-described amplification oligonucleotides under amplification conditions. In another embodiment, the method comprises contacting the test sample with at least one of the above-described detection probes and at least two of the above-described capture probes under stringent conditions, and at least one of the above-described amplification oligonucleotides under amplification conditions. In another embodiment, the method comprises contacting the test sample with at least one of the above-described detection probes and at least two of the above-described capture probes under stringent conditions, and at least two of the above-described amplification oligonucleotides under amplification conditions.

The disclosure also contemplates kits for determining whether *T. vaginalis* is present in a test sample. These kits comprise at least one of the above-described detection probes specific for *T. vaginalis* derived nucleic acid and optionally include written instructions for determining the presence or amount of *T. vaginalis* in a test sample. In another embodiment, the kits also include at least one of the above-described amplification oligonucleotides appropriate for amplifying the target sequence or its complement. In yet another embodiment, the kits also include at least one of the above-described capture probes for separating the target nucleic acid from other components of the test sample prior to amplifying or directly detecting the target sequence or its complement.

Those skilled in the art will appreciate that the detection probes of the present disclosure may be used as amplification oligonucleotides or capture probes, the amplification oligonucleotides may be used a detection probes or capture probes, and the capture probes may be used as amplification oligonucleotides or detection probes depending upon the degree of specificity required. Other features and advantages of the disclosure will be apparent from the following description of the embodiments thereof and from the claims.

DESCRIPTION OF THE EMBODIMENTS

The present disclosure describes oligonucleotides targeted to nucleic acids derived from *T. vaginalis* which are particularly useful for determining the presence or absence of *T. vaginalis* in a test sample. The oligonucleotides can aid in detecting *T. vaginalis* in different ways, such as by functioning as detection probes, capture probes, and/or amplification oligonucleotides. Detection probes of the present disclosure can preferentially hybridize to a target nucleic acid sequence present in a target nucleic acid derived from *T. vaginalis* under stringent hybridization conditions to form detectable duplexes which indicate the presence of *T. vaginalis* in a test sample. Probes of the present disclosure are believed to be capable of distinguishing between *T. vaginalis* and its known closest phylogenetic neighbor. Capture probes of the present disclosure can hybridize to a target nucleic acid sequence present in nucleic acid derived from *T. vaginalis* under assay conditions and can be used to separate target nucleic acid from other components of a clinical specimen. Amplification oligonucleotides of the present disclosure can hybridize to a target nucleic acid sequence present in nucleic acid derived from *T. vaginalis* under amplification conditions and can be used, for example, as primers in amplification reactions to generate multiple copies of *T. vaginalis*-derived nucleic acid. The probes and amplification oligonucleotides can be used in assays for the detection and/or quantitation of *T. vaginalis* in a test sample.

A. Definitions

The following terms have the indicated meanings in the specification unless expressly indicated to have a different meaning.

By "sample" or "test sample" is meant any substance suspected of containing a target organism or nucleic acid derived from the target organism. The substance may be, for example, an unprocessed clinical specimen, such as a genitourinary tract specimen, a buffered medium containing the specimen, a medium containing the specimen and lytic agents for releasing nucleic acid belonging to the target organism, or a medium containing nucleic acid derived from the target organism which has been isolated and/or purified in a reaction receptacle or on a reaction material or device. In the claims, the terms "sample" and "test sample" may refer to specimen in its raw form or to any stage of processing to release, isolate and purify nucleic acid derived from target organisms in the specimen. Thus, within a method of use claim, each reference to a "sample" or "test sample" may refer to a substance suspected of containing nucleic acid derived from the target organism or organisms at different stages of processing and is not limited to the initial form of the substance in the claim.

By "target nucleic acid" or "target" is meant a nucleic acid containing a target nucleic acid sequence.

By "target nucleic acid sequence," "target sequence" or "target region" is meant a specific deoxyribonucleotide or ribonucleotide sequence comprising all or part of the nucleotide sequence of a single-stranded nucleic acid molecule.

By "oligonucleotide" or "oligomer" is meant a polymer made up of two or more nucleoside subunits or nucleobase subunits coupled together. The oligonucleotide may be DNA and/or RNA and analogs thereof. The sugar groups of the nucleoside subunits may be ribose, deoxyribose and analogs thereof, including, for example, ribonucleosides having a 2'-O-methylsubstitution to the ribofuranosyl moiety. (Oligonucleotides including nucleoside subunits having 2' substitutions and which are useful as detection probes, capture probes, and/or amplification oligonucleotides are disclosed by Becker et al., "Method for Amplifying Target Nucleic Acids Using Modified Primers," U.S. Pat. No. 6,130,038.) The nucleoside subunits may be joined by linkages such as phosphodiester linkages, modified linkages, or by non-nucleotide moieties which do not prevent hybridization of the oligonucleotide to its complementary target nucleic acid sequence. Modified linkages include those linkages in which a standard phosphodiester linkage is replaced with a different linkage, such as a phosphorothioate linkage or a methylphosphonate linkage. The nucleobase subunits may be joined, for example, by replacing the natural deoxyribose phosphate backbone of DNA with a pseudo-peptide backbone, such as a 2-aminoethylglycine backbone which couples the nucleobase subunits by means of a carboxymethyl linker to the central secondary amine. (DNA analogs having a pseudo-peptide backbone are commonly referred to as "peptide nucleic acids" or "PNA", and are disclosed by Nielsen et al., "Peptide Nucleic Acids," U.S. Pat. No. 5,539,082.) Other non-limiting examples of oligonucleotides or oligomers contemplated by the present disclosure include nucleic acid analogs containing bicyclic and tricyclic nucleoside and nucleotide analogs referred to as "Locked Nucleic Acids," "Locked Nucleoside Analogues" or "LNA." (Locked Nucleic Acids are disclosed by Wang, "Conformationally Locked Nucleosides and Oligonucleotides," U.S. Pat. No. 6,083,482; Imanishi et al., "Bicyclonucleoside and Oligonucleotide Analogues," U.S. Pat. No. 6,268,490; and Wengel et al., "Oligonucleotide Analogues," U.S. Pat. No. 6,670,461.) Any nucleic acid analog is contemplated by the present disclosure, provided that the modified oligonucleotide can hybridize to a target nucleic acid under stringent hybridization conditions or amplification conditions. In the case of detection probes, the modified oligonucleotides must also be capable of preferentially hybridizing to the target nucleic acid under stringent hybridization conditions.

Oligonucleotides of a defined sequence may be produced by techniques known to those of ordinary skill in the art, such as by chemical or biochemical synthesis, and by in vitro or in vivo expression from recombinant nucleic acid molecules, e.g., bacterial or retroviral vectors. As intended by this disclosure, an oligonucleotide does not consist of wild-type chromosomal DNA or the in vivo transcription products thereof. One use of an oligonucleotide is as a detection probe. Oligonucleotides may also be used as capture probes and amplification oligonucleotides.

By "detection probe" or "probe" is meant a structure comprising an oligonucleotide having a base sequence sufficiently complementary to its target nucleic acid sequence to form a probe:target hybrid stable for detection under stringent hybridization conditions. As would be understood by someone having ordinary skill in the art, the oligonucleotide is an isolated nucleic acid molecule, or an analog thereof, in a form not found in nature without human intervention (e.g., recombined with foreign nucleic acid, isolated, or purified to some extent). The probes of this disclosure may have additional nucleosides or nucleobases complementary to nucleotides outside of the targeted region so long as such nucleosides or nucleobases do not prevent hybridization under stringent hybridization conditions and, in the case of detection probes, do not prevent preferential hybridization to the target nucleic acid. A non-complementary sequence may also be included, such as a target capture sequence (generally a homopolymer tract, such as a poly-A, poly-T or poly-U tail), promotor sequence, a binding site for RNA transcription, a restriction endonuclease recognition site, or sequences which will confer a desired secondary or tertiary structure, such as a catalytic active site or a hairpin structure, which can be used to facilitate detection and/or amplification. Probes of a defined sequence may be produced by techniques known to those of ordinary skill in the art, such as by chemical synthesis, and by in vitro or in vivo expression from recombinant nucleic acid molecules.

By "stable" or "stable for detection" is meant that the temperature of a reaction mixture is at least 2° C. below the melting temperature of a nucleic acid duplex. The temperature of the reaction mixture is more at least 5° C. below the melting temperature of the nucleic acid duplex in one embodiment, or even more at least 10° C. below the melting temperature of the reaction mixture in another embodiment.

By "RNA and DNA equivalents" is meant RNA and DNA molecules having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "hybridization" or "hybridize" is meant the ability of two completely or partially complementary nucleic acid strands to come together under specified hybridization assay conditions in a parallel or antiparallel orientation to form a stable structure having a double-stranded region. The two constituent strands of this double-stranded structure, sometimes called a hybrid, are held together by hydrogen bonds. Although these hydrogen bonds most commonly form between nucleotides containing the bases adenine and thymine or uracil (A and T or U) or cytosine and guanine (C and G) on single nucleic acid strands, base pairing can also form between bases which are not members of these "canonical" pairs. Non-canonical base pairing is well-known in the art. (See, e.g., Roger L. P. Adams et al., The Biochemistry of the Nucleic Acids (11$^{th}$ ed. 1992).)

By "preferentially hybridize" is meant that under stringent hybridization conditions, detection probes can hybridize to their target nucleic acids to form stable probe:target hybrids indicating the presence of at least one organism of interest, and there is not formed a sufficient number of stable probe:non-target hybrids to indicate the presence of non-targeted organisms, especially phylogenetically closely related organisms. Thus, the probe hybridizes to target nucleic acid to a sufficiently greater extent than to non-target nucleic acid to enable one having ordinary skill in the art to accurately detect the presence (or absence) of nucleic acid derived from *T. vaginalis*, as appropriate, and distinguish its presence from that of a phylogenetically closely related organism in a test sample. In general, reducing the degree of complementarity between an oligonucleotide sequence and its target sequence will decrease the degree or rate of hybridization of the oligonucleotide to its target region. However, the inclusion of one or more non-complementary nucleosides or nucleobases may facilitate the ability of an oligonucleotide to discriminate against non-target organisms.

Preferential hybridization can be measured using techniques known in the art and described herein, such as in the examples provided below. Some embodiments of preferential hybridization include when there is at least a 10-fold difference between target and non-target hybridization signals in a test sample, or when there is at least a 100-fold difference, or when there is at least a 1,000-fold difference. In general, non-target hybridization signals in a test sample are no more than the background signal level.

By "stringent hybridization conditions" or "stringent conditions" is meant conditions permitting a detection probe to preferentially hybridize to a target nucleic acid (for example, rRNA or rDNA derived from *T. vaginalis*) and not to nucleic acid derived from a closely related non-target microorganism. Stringent hybridization conditions may vary depending upon factors including the GC content and length of the probe, the degree of similarity between the probe sequence and sequences of non-target sequences which may be present in the test sample, and the target sequence. Hybridization conditions include the temperature and the composition of the hybridization reagents or solutions. Specific hybridization assay conditions are set forth infra in the Examples section and in the section entitled "Detection Probes to *Trichomonas vaginalis* Ribosomal Nucleic Acid." Exemplary hybridization conditions for detecting target nucleic acids derived from *T. vaginalis* with the probes of the present disclosure include a temperature of about 60° C. and a salt concentration of about 1.5 M. Other acceptable stringent hybridization conditions could be easily ascertained by someone having ordinary skill in the art.

By "assay conditions" is meant conditions permitting stable hybridization of an oligonucleotide to a target nucleic acid. Assay conditions do not require preferential hybridization of the oligonucleotide to the target nucleic acid.

By "nucleic acid duplex," "duplex," "nucleic acid hybrid" or "hybrid" is meant a stable nucleic acid structure comprising a double-stranded, hydrogen-bonded region. Such hybrids include RNA:RNA, RNA:DNA and DNA:DNA duplex molecules and analogs thereof. The structure is sufficiently stable to be detectable by any known means, including means that do not require a probe associated label. For instance, the detection method may include a probe-coated substrate that is optically active and sensitive to changes in mass at its surface. Mass changes result in different reflective and transmissive properties of the optically active substrate in response to light and serve to indicate the presence or amount of immobilized target nucleic acid. (This exemplary form of optical detection is disclosed by Nygren et al., "Devices and Methods for Optical Detection of Nucleic Acid Hybridization," U.S. Pat. No. 6,060,237.) Other means for detecting the formation of a nucleic acid duplex that do not require the use of a labeled probe include the use of binding agents, which include intercalating agents such as ethidium bromide. See, e.g., Higuchi, "Homogenous Methods for Nucleic Amplification and Detection," U.S. Pat. No. 5,994,056.

By "amplification oligonucleotide" or "primer" is meant an oligonucleotide capable of hybridizing to a target nucleic acid and acting as a primer and/or a promoter template (e.g., for synthesis of a complementary strand, thereby forming a functional promoter sequence) for the initiation of nucleic acid synthesis. If the amplification oligonucleotide is designed to initiate RNA synthesis, the primer may contain a base sequence which is non-complementary to the target sequence but which is recognized by a RNA polymerase such as a T7, T3, or SP6 RNA polymerase. An amplification oligonucleotide may contain a 3' terminus that is modified to prevent or lessen the rate or amount of primer extension. (McDonough et al., "Methods of Amplifying Nucleic Acids Using Promoter-Containing Primer Sequences," U.S. Pat. No. 5,766,849, disclose primers and promoter-primers having modified or blocked 3'-ends.) While the amplification oligonucleotides of the present disclosure may be chemically synthesized or derived from a vector, they are not naturally occurring nucleic acid molecules.

By "nucleic acid amplification" or "target amplification" is meant increasing the number of nucleic acid molecules having at least one target nucleic acid sequence. Target amplification according to the present disclosure may be either linear or exponential.

By "amplification conditions" is meant conditions permitting nucleic acid amplification. Acceptable amplification conditions could be readily ascertained without the exercise of anything more than routine experimentation by someone having ordinary skill in the art depending on the particular method of amplification employed.

By "antisense," "opposite sense," or "negative sense" is meant a nucleic acid molecule perfectly complementary to a reference, or sense, nucleic acid molecule.

By "sense," "same-sense," or "positive sense" is meant a nucleic acid molecule perfectly homologous to a reference nucleic acid molecule.

By "amplicon" is meant a nucleic acid molecule generated in a nucleic acid amplification reaction and which is derived from a target nucleic acid. An amplicon contains a target nucleic acid sequence that may be of the same or opposite sense as the target nucleic acid.

By "derived" is meant that the referred to nucleic acid is obtained directly from an organism or is the product of a nucleic acid amplification. Thus, a nucleic acid that is "derived" from an organism may be, for example, an antisense RNA molecule which does not naturally exist in the organism.

By "capture probe" is meant an oligonucleotide that is capable of binding to a target nucleic acid (generally in a region other than that targeted by a detection probe) and, either directly or indirectly, to a solid support, thereby providing means for immobilizing and isolating the target nucleic acid in a test sample. The capture probe includes a target-complementary base sequence that hybridizes to the target nucleic acid. In one embodiment the capture probes may include a member of ligand-ligate binding pair (e.g., avidin-biotin linkage) for immobilizing the capture probe on a solid support. In another embodiment the capture probes include an immobilized probe binding region that hybridizes to an immobilized probe bound to a solid support. While the capture probe hybridizes to both the target nucleic acid and the immobilized probe under stringent conditions, the target-complementary base sequence and the immobilized probe binding regions of the capture probe may be designed to bind to their target sequences under different hybridization conditions. In this way, the capture probe may be designed so that it first hybridizes to the target nucleic acid under more favorable in solution kinetics before adjusting the conditions to permit hybridization of the immobilized probe binding region to the immobilized probe. The target-complementary base sequence and immobilized probe binding regions may be contained within the same oligonucleotide, directly adjoining each other or separated by one or more optionally modified nucleotides, or these regions may be joined to each other by means of a non-nucleotide linker.

By "target-complementary base sequence" is meant that portion of an oligonucleotide which stably binds to a target sequence present in a target nucleic acid, or the complement of the target sequence, under assay conditions. The assay conditions may be stringent hybridization conditions or amplification conditions.

By "non-complementary" is meant that portion of an oligonucleotide which does not stably bind to a target sequence present in a target nucleic acid, or the complement of the target sequence, under assay conditions. The assay conditions may be stringent hybridization conditions or amplification conditions.

By "immobilized probe binding region" is meant that portion of an oligonucleotide which hybridizes to an immobilized probe under assay conditions.

By "homopolymer" tail in the claims is meant a contiguous base sequence of at least 10 identical bases (e.g., 10 contiguous adenines or thymines).

By "immobilized probe" is meant an oligonucleotide for joining a capture probe to an immobilized support. The immobilized probe is joined either directly or indirectly to the solid support by a linkage or interaction which remains stable under the conditions employed to hybridize the capture probe to the target nucleic acid and to the immobilized probe, whether those conditions are the same or different. The immobilized probe facilitates separation of the bound target nucleic acid from unbound materials in a sample.

By "isolate" or "isolating" is meant that at least a portion of the target nucleic acid present in a test sample is concentrated within a reaction receptacle or on a reaction device or solid carrier (e.g., test tube, cuvette, microtiter plate well, nitrocellulose filter, slide or pipette tip) in a fixed or releasable manner so that the target nucleic acid can be purified without significant loss of the target nucleic acid from the receptacle, device or carrier.

By "purify" or "purifying" is meant that one or more components of the test sample are removed from one or more other components of the sample. Sample components to be purified may include viruses, nucleic acids or, in particular, target nucleic acids in a generally aqueous solution phase which may also include undesirable materials such as proteins, carbohydrates, lipids, non-target nucleic acid and/or labeled probes. In some embodiments, the purifying step removes at least about 70%, or at least about 90%, or at least about 95% of the undesirable components present in the sample.

By "phylogenetically closely related" is meant that the organisms are closely related to each other in an evolutionary sense and therefore would be expected to have a higher total nucleic acid sequence homology than organisms that are more distantly related. Organisms occupying adjacent and next to adjacent positions on the phylogenetic tree are closely related. Organisms occupying positions farther away than adjacent or next to adjacent positions on the phylogenetic tree will still be closely related if they have significant total nucleic acid sequence homology.

B. Hybridization Conditions and Probe Design

Hybridization reaction conditions, most importantly the temperature of hybridization and the concentration of salt in the hybridization solution, can be selected to allow the detection probes or, in some cases, amplification oligonucleotides of the present disclosure to preferentially hybridize to a *T. vaginalis*-derived target nucleic acid and not to other non-target nucleic acids suspected of being present in a test sample. At decreased salt concentrations and/or increased temperatures (conditions of increased stringency) the extent of nucleic acid hybridization decreases as hydrogen bonding between paired nucleobases in the double-stranded hybrid molecule is disrupted. This process is known as "melting."

Generally speaking, the most stable hybrids are those having the largest number of contiguous, perfectly matched (i.e., hydrogen-bonded) nucleotide base pairs. Such hybrids would usually be expected to be the last to melt as the stringency of the hybridization conditions increases. However, a double-stranded nucleic acid region containing one or more mismatched, "non-canonical," or imperfect base pairs (resulting in weaker or non-existent base pairing at that position in the nucleotide sequence of a nucleic acid) may still be sufficiently stable under conditions of relatively high stringency to allow the nucleic acid hybrid to be formed and detected in a hybridization assay without cross-reacting with other, non-selected nucleic acids which may be present in a test sample.

Hence, depending on the degree of similarity between the nucleotide sequences of the target nucleic acid and those of non-target nucleic acids belonging to phylogenetically distinct, but closely-related organisms on one hand, and the degree of complementarity between the nucleotide sequences of a particular detection probe or amplification oligonucleotide and those of the target and non-target nucleic acids on the other, one or more mismatches will not necessarily defeat the ability of an oligonucleotide contained in the probe or amplification oligonucleotide to hybridize to the target nucleic acid and not to non-target nucleic acids.

The detection probes of the present disclosure were chosen, selected, and/or designed to maximize the difference between the melting temperatures of the probe:target hybrid ($T_m$, defined as the temperature at which half of the potentially double-stranded molecules in a given reaction mixture are in a single-stranded, denatured state) and the $T_m$ of a mismatched hybrid formed between the probe and ribosomal RNA (rRNA) or ribosomal DNA (rDNA) of the phylogenetically most closely-related organisms expected to be present in the test sample, but not sought to be detected. While the unlabeled amplification oligonucleotides and capture probes need not have such an extremely high degree of specificity as the detection probe to be useful in the present disclosure, they are designed in a similar manner to preferentially hybridize to one or more target nucleic acids over other nucleic acids under specified amplification, assay or stringent hybridization conditions.

To facilitate the identification of nucleic acid sequences to be used in the design of probes, nucleotide sequences from different organisms were first aligned to maximize homology. The source organisms and the associated nucleotide sequences used for this comparison were obtained from the GenBank database and had the following accession numbers: *Trichomonas vaginalis* (Accession No. U17510), *Trimastix pyriformis* (Accession No. AF244903), *Dientamoeba fragilis* (Accession No. U37461), *Trichomonas gallinae* (Accession No. U86614), *Trichomonas tenax* (Accession Nos. D49495 and U37711), *Tetratrichomonas gallinarum* (Accession No. AF124608), *Kalotermes flavicollis* (Accession No. AF215856), *Trichomitus trypanoides* (Accession No. X79559), *Hodotermopsis sjoestedti* (Accession No. AB032234), *Pentatrichomonas hominis* (Accession No. AF124609), *Pseudotrypanosoma giganteum* (Accession No. AF052706), *Ditrichomonas honigbergi* (Accession No. U17505), *Monotrichomonas* species ATCC No. 50693 (Accession No. AF072905), *Pseudotrichomonas keilini* (Accession No. U17511), *Monocercomonas* species ATCC No. 50210 (Accession No. U17507), *Tritrichomonas foetus* (Accession No. U17509) and *Entamoeba histolytica* (Accession No. X64142).

Within the rRNA molecule there is a close relationship between secondary structure (caused in part by intra-molecular hydrogen bonding) and function. This fact imposes restrictions on evolutionary changes in the primary nucleotide sequence causing the secondary structure to be maintained. For example, if a base is changed in one "strand" of a double helix (due to intra-molecular hydrogen bonding, both "strands" are part of the same rRNA molecule), a compensating substitution usually occurs in the primary sequence of the other "strand" in order to preserve complementarity (this is referred to as co-variance), and thus the necessary secondary structure. This allows two very different rRNA sequences to be aligned based both on the conserved primary sequence and also on the conserved secondary structure elements. Potential target sequences for the detection probes described herein were identified by noting variations in the homology of the aligned sequences.

The sequence evolution at each of the variable regions is mostly divergent. Because of the divergence, corresponding rRNA variable regions of more distant phylogenetic relatives of *T. vaginalis* show greater differences from *T. vaginalis* rRNA than do the rRNAs of phylogenetically closer relatives. Sufficient variation between *T. vaginalis* and other organisms was observed to identify potential target sites and to design detection probes useful for distinguishing *T. vaginalis* over non-*T. vaginalis* organisms in a test sample, particularly *Trichomonas tenax*, the most closely related organism to *T. vaginalis*.

Merely identifying putatively unique potential target nucleotide sequences does not guarantee that a functionally species-specific detection probe may be made to hybridize to *T. vaginalis* rRNA or rDNA comprising that sequence. Various other factors will determine the suitability of a nucleic acid locus as a target site for genus-specific or species-specific probes. Because the extent and specificity of hybridization reactions such as those described herein are affected by a number of factors, manipulation of one or more of those factors will determine the exact sensitivity and specificity of a particular oligonucleotide, whether perfectly complementary to its target or not. The importance and effect of various assay conditions are known to those skilled in the art and are disclosed by Hogan et al., "Nucleic Acid Probes for Detection and/or Quantitation of Non-Viral Organisms," U.S. Pat. No. 5,840,488; Hogan et al., "Nucleic Acid Probes to *Mycobac-*

*terium gordonae*," U.S. Pat. No. 5,216,143; and Kohne, "Method for Detection, Identification and Quantitation of Non-Viral Organisms," U.S. Pat. No. 4,851,330. The contents of each of the foregoing references is hereby incorporated by reference herein.

The desired temperature of hybridization and the hybridization solution composition (such as salt concentration, detergents, and other solutes) can also greatly affect the stability of double-stranded hybrids. Conditions such as ionic strength and the temperature at which a probe will be allowed to hybridize to a target must be taken into account in constructing a genus-specific or species-specific probe. The thermal stability of hybrid nucleic acids generally increases with the ionic strength of the reaction mixture. On the other hand, chemical reagents that disrupt hydrogen bonds, such as formamide, urea, dimethyl sulfoxide and alcohols, can greatly reduce the thermal stability of the hybrids.

To maximize the specificity of a probe for its target, the subject probes of the present disclosure were designed to hybridize to their targets under conditions of high stringency. Under such conditions only single nucleic acid strands having a high degree of complementarity will hybridize to each other. Single nucleic acid strands without such a high degree of complementarity will not form hybrids. Accordingly, the stringency of the assay conditions determines the amount of complementarity that should exist between two nucleic acid strands in order to form a hybrid. Stringency is chosen to maximize the difference in stability between the hybrid formed between the probe and the target nucleic acid and potential hybrids between the probe and any non-target nucleic acids present in a test sample.

Proper specificity may be achieved by minimizing the length of the detection probe having perfect complementarity to sequences of non-target organisms, by avoiding G and C rich regions of complementarity to non-target nucleic acids, and by constructing the probe to contain as many destabilizing mismatches to non-target sequences as possible. Whether a probe is appropriate for detecting only a specific type of organism depends largely on the thermal stability difference between probe:target hybrids versus probe:non-target hybrids. In designing probes, the differences in these $T_m$ values should be as large as possible (for example, 2-5° C. or more). Manipulation of the $T_m$ can be accomplished by changes to probe length and probe composition (e.g., GC content versus AT content).

In general, the optimal hybridization temperature for oligonucleotide probes is approximately 5° C. below the melting temperature for a given duplex. Incubation at temperatures below the optimum temperature may allow mismatched base sequences to hybridize and can therefore decrease specificity. The longer the probe, the more hydrogen bonding between base pairs and, in general, the higher the $T_m$. Increasing the percentage of G and C also increases the $T_m$ because G-C base pairs exhibit additional hydrogen bonding and therefore greater thermal stability than A-T base pairs. Such considerations are known in the art. (See, e.g., J. Sambrook et al., Molecular Cloning: A Laboratory Manual, ch. 11 ($2^{nd}$ ed. 1989).)

One method to determine $T_m$, measures hybridization using the well known Hybridization Protection Assay (HPA) disclosed by Arnold et al., "Homogenous Protection Assay," U.S. Pat. No. 5,283,174, the contents of which are hereby incorporated by reference herein. The $T_m$ can be measured using HPA in the following manner. Probe molecules are labeled with an acridinium ester and permitted to form probe: target hybrids in a lithium succinate buffer (0.1 M lithium succinate buffer, pH 4.7, 20 mM EDTA, 15 mM aldrithiol-2, 1.2 M LiCl, 3% (v/v) ethanol absolute, 2% (w/v) lithium lauryl sulfate) using an excess amount of target. Aliquots of the solution containing the probe:target hybrids are then diluted in the lithium succinate buffered solution and incubated for five minutes at various temperatures starting below that of the anticipated $T_m$ (typically 55° C.) and increasing in 2-5° C. increments. This solution is then diluted with a mild alkaline borate buffer (600 mM boric acid, 240 mM NaOH, 1% (v/v) TRITON® X-100 detergent, pH 8.5) and incubated at an equal or lower temperature (for example 50° C.) for ten minutes.

Under these conditions the acridinium ester attached to the single-stranded probe is hydrolyzed, while the acridinium ester attached to hybridized probe is relatively protected from hydrolysis. Thus, the amount of acridinium ester remaining after hydrolysis treatment is proportional to the number of hybrid molecules. The remaining acridinium ester can be measured by monitoring the chemiluminescence produced from the remaining acridinium ester by adding hydrogen peroxide and alkali to the solution. Chemiluminescence can be measured in a luminometer, such as a LEADER® Luminometer (Gen-Probe Incorporated; San Diego, Calif.). The resulting data is plotted as percent of maximum signal (usually from the lowest temperature) versus temperature. The $T_m$ is defined as the temperature at which 50% of the maximum signal remains. In addition to the method above, $T_m$ may be determined by isotopic methods known to those skilled in the art (see, e.g., Hogan et al., U.S. Pat. No. 5,840,488).

To ensure specificity of a detection probe for its target, it is preferable to design probes that hybridize only to target nucleic acid under conditions of high stringency. Only highly complementary sequences will form hybrids under conditions of high stringency. Accordingly, the stringency of the assay conditions determines the amount of complementarity needed between two sequences in order for a stable hybrid to form. Stringency should be chosen to maximize the difference in stability between the probe:target hybrid and potential probe:non-target hybrids.

Examples of specific stringent hybridization conditions are provided in the Examples section infra. Of course, alternative stringent hybridization conditions can be determined by those of ordinary skill in the art based on the present disclosure. (See, e.g., Sambrook et al., supra, ch. 11.)

The length of the target nucleic acid sequence region and, accordingly, the length of the probe sequence can also be important. In some cases, there may be several sequences from a particular region, varying in location and length, which may be used to design probes with the desired hybridization characteristics. In other cases, one probe may be significantly better with regard to specificity than another that differs from it merely by a single base. While it is possible for nucleic acids that are not perfectly complementary to hybridize, the longest stretch of perfectly complementary bases, as well as the base compositions, will generally determine hybrid stability.

Regions of rRNA known to form strong internal structures inhibitory to hybridization are less preferred target regions. Likewise, probes with extensive self-complementarity are generally to be avoided, with specific exceptions being discussed below. If a strand is wholly or partially involved in an intramolecular or intermolecular hybrid, it will be less able to participate in the formation of a new intermolecular probe: target hybrid without a change in the reaction conditions. Ribosomal RNA molecules are known to form very stable intramolecular helices and secondary structures by hydrogen bonding. By designing a probe to a region of the target nucleic acid which remains substantially single-stranded under hybridization conditions, the rate and extent of hybridization between probe and target may be increased.

A genomic ribosomal nucleic acid (rDNA) target occurs naturally in a double-stranded form, as does the product of the polymerase chain reaction (PCR). These double-stranded targets are naturally inhibitory to hybridization with a probe and require denaturation prior to hybridization. Appropriate denaturation and hybridization conditions are known in the art (see, e.g., Southern, E. M., *J. Mol. Biol.*, 98:503 (1975)).

A number of formulae are available which will provide an estimate of the melting temperature for perfectly matched oligonucleotides to their target nucleic acids. One such formula is the following: $T_m = 81.5 + 16.6 \ (\log_{10}[\text{Na}+]) + 0.41$ (fraction G+C)−(600/N) (where N=the length of the oligonucleotide in number of nucleotides) provides a good estimate of the $T_m$ oligonucleotides between 14 and 60 to 70 nucleotides in length. From such calculations, subsequent empirical verification or "fine tuning" of the $T_m$ may be made using screening techniques well known in the art. For further information on hybridization and oligonucleotide probes reference may be made to Sambrook et al., supra, ch. 11. This reference, among others well known in the art, also provides estimates of the effect of mismatches on the $T_m$, of a hybrid. Thus, from the known nucleotide sequence of a given region of the ribosomal RNA (or rDNA) of two or more organisms, oligonucleotides may be designed which will distinguish these organisms from one another.

C. Nucleic Acid Amplification

Amplification oligonucleotides of the present disclosure may be oligodeoxynucleotides and are sufficiently long to be used as a substrate for the synthesis of extension products by a nucleic acid polymerase. Optimal amplification oligonucleotide length should take into account several factors, including the temperature of reaction, the structure and base composition of the amplification oligonucleotide, and how the amplification oligonucleotide is to be used. For example, for optimal specificity the oligonucleotide amplification oligonucleotide generally should be at least 12 bases in length, depending on the complexity of the target nucleic acid sequence. If such specificity is not essential, shorter amplification oligonucleotides may be used. In such a case, it may be desirable to carry out the reaction at cooler temperatures in order to form stable hybrid complexes with the template nucleic acid.

Useful guidelines for designing amplification oligonucleotides and detection probes with desired characteristics are described infra in the section entitled "Preparation of Oligonucleotides." Optimal sites for amplifying and probing contain at least two or three conserved regions of *T. vaginalis* nucleic acid. These regions are about 15 to 350 bases in length in one embodiment, or between about 15 and 150 bases in length in another embodiment.

The degree of amplification observed with a set of amplification oligonucleotides (e.g., primers and/or promoter-primers) depends on several factors, including the ability of the amplification oligonucleotides to hybridize to their specific target sequences and their ability to be extended or copied enzymatically. While amplification oligonucleotides of different lengths and base compositions may be used, amplification oligonucleotides in this disclosure have target-complementary base sequences of 18 to 40 bases with a predicted $T_m$ to target of about 42° C.

Parameters affecting probe hybridization, such as $T_m$, complementarity, and secondary structure of the target sequence, also affect amplification oligonucleotide hybridization and therefore performance of the amplification oligonucleotides. The degree of non-specific extension (primer-dimer or non-target copying) can also affect amplification efficiency. Thus, amplification oligonucleotides are selected to have low self-complementarity or cross-complementarity, particularly at the 3' ends of their sequences. Notwithstanding, it should be noted that the "signal primers" described infra could be modified to include regions of self-complementarity, thereby transforming them into "molecular torch" or "molecular beacon" signal primers, such as these terms are defined below. Lengthy homopolymer runs and high GC content are avoided to reduce spurious primer extension. Computer programs are available to aid in this aspect of the design, including Oligo Tech analysis software which is available from Oligos Etc. Inc. of Wilsonville, Oreg.

A nucleic acid polymerase used in conjunction with the amplification oligonucleotides of the present disclosure refers to a chemical, physical, or biological agent that incorporates either ribonucleotides or deoxyribonucleotides, or both, into a nucleic acid polymer, or strand, in a template-dependent manner. Examples of nucleic acid polymerases include DNA-directed DNA polymerases, RNA-directed DNA polymerases, and RNA-directed RNA polymerases. DNA polymerases bring about nucleic acid synthesis in a template-dependent manner and in a 5' to 3' direction. Because of the typical anti-parallel orientation of the two strands in a double-stranded nucleic acid, this direction is from a 3' region on the template to a 5' region on the template. Examples of DNA-directed DNA polymerases include *E. coli* DNA polymerase I, the thermostable DNA polymerase from *Thermus aquaticus* (Taq), and the large fragment of DNA polymerase I from *Bacillus stearothermophilis* (Bst). Examples of RNA directed DNA polymerases include various retroviral reverse transcriptases, such as Moloney murine leukemia virus (MMLV) reverse transcriptase or avian myeloblastosis virus (AMV) reverse transcriptase.

During most nucleic acid amplification reactions, a nucleic acid polymerase adds nucleotide residues to the 3' end of the primer using the target nucleic acid as a template, thus synthesizing a second nucleic acid strand having a nucleotide sequence partially or completely complementary to a region of the target nucleic acid. In many nucleic acid amplification reactions, the two strands comprising the resulting double-stranded structure must be separated by chemical or physical means in order to allow the amplification reaction to proceed. Alternatively, the newly synthesized template strand may be made available for hybridization with a second primer or promoter-primer by other means, such as through strand displacement or the use of a nucleolytic enzyme which digests part or all of the original target strand. In this way the process may be repeated through a number of cycles, resulting in a large increase in the number of nucleic acid molecules having the target nucleotide sequence.

Either the first or second amplification oligonucleotide, or both, may be a promoter-primer. (In some applications, the amplification oligonucleotides may only consist of promoter-primers which are complementary to the sense strand, as disclosed by Kacian et al., "Nucleic Acid Sequence Amplification Method, Composition and Kit," U.S. Pat. No. 5,554, 516.) A promoter-primer usually contains an oligonucleotide that is not complementary to a nucleotide sequence present in the target nucleic acid molecule or primer extension product(s) (see Kacian et al., "Nucleic Acid Sequence Amplification Methods," U.S. Pat. No. 5,399,491, for a description of such oligonucleotides). These non-complementary sequences may be located 5' to the complementary sequences on the amplification oligonucleotide and may provide a locus for initiation of RNA synthesis when made double-stranded through the action of a nucleic acid polymerase. The promoter thus provided may allow for the in vitro transcription of multiple RNA copies of the target nucleic acid sequence. It will be appreciated that when reference is made to a primer in this specification, such reference is intended to include the primer aspect of a promoter-primer as well, unless the context of the reference clearly indicates otherwise.

In some amplification systems (see, e.g., the amplification methods disclosed by Dattagupta et al., "Isothermal Strand Displacement Amplification," U.S. Pat. No. 6,087,133), the amplification oligonucleotides may contain 5' non-complementary nucleotides which assist in strand displacement. Furthermore, when used in conjunction with a nucleic acid polymerase having 5' exonuclease activity, the amplification oligonucleotides may have modifications at their 5' end to prevent enzymatic digestion. Alternatively, the nucleic acid polymerase may be modified to remove the 5' exonuclease activity, such as by treatment with a protease that generates an active polymerase fragment with no such nuclease activity. In such a case the primers need not be modified at their 5' ends.

1. Preparation of Oligonucleotides

The detection probes, capture probes, and amplification oligonucleotides of the present disclosure can be readily prepared by methods known in the art. In one embodiment, the oligonucleotides are synthesized using solid phase methods. For example, Caruthers describes using standard phosphoramidite solid-phase chemistry to join nucleotides by phosphodiester linkages. See Caruthers et al., "Chemical Synthesis of Deoxynucleotides by the Phosphoramidite Method," *Methods Enzymol.*, 154:287 (1987). Automated solid-phase chemical synthesis using cyanoethyl phosphoramidite precursors has been described by Barone. See Barone et al., "In Situ Activation of bis-dialkylaminephosphines—a New Method for Synthesizing Deoxyoligonucleotides on Polymer Supports," *Nucleic Acids Res.*, 12(10):4051 (1984). Likewise, Batt, "Method and Reagent for Sulfurization of Organophosphorous Compounds," U.S. Pat. No. 5,449,769, discloses a procedure for synthesizing oligonucleotides containing phosphorothioate linkages. In addition, Riley et al., "Process for the Purification of Oligomers," U.S. Pat. No. 5,811,538 disclose the synthesis of oligonucleotides having different linkages, including methylphosphonate linkages. Moreover, methods for the organic synthesis of oligonucleotides are known to those of skill in the art and are described in, for example, Sambrook et al., supra, ch. 10.

Following synthesis of a particular oligonucleotide, several different procedures may be utilized to purify and control the quality of the oligonucleotide. Suitable procedures include polyacrylamide gel electrophoresis or high pressure liquid chromatography. Both of these procedures are well known to those skilled in the art.

All of the oligonucleotides of the present disclosure, whether detection probes, capture probes or amplification oligonucleotides, may be modified with chemical groups to enhance their performance or to facilitate the characterization of amplification products.

For example, backbone-modified oligonucleotides such as those having phosphorothioate, methylphosphonate, 2'-O-alkyl, or peptide groups which render the oligonucleotides resistant to the nucleolytic activity of certain polymerases or to nuclease enzymes may allow the use of such enzymes in an amplification or other reaction. Another example of a modification involves using non-nucleotide linkers incorporated between nucleotides in the nucleic acid chain of a probe or primer, and which do not prevent hybridization of a probe or hybridization and elongation of a primer. (See Arnold et al., "Non-Nucleotide Linking Reagents for Nucleotide Probes," U.S. Pat. No. 6,031,091, the contents of which are hereby incorporated by reference herein.) The oligonucleotides of the present disclosure may also contain mixtures of the desired modified and natural nucleotides.

The 3' end of an amplification oligonucleotide, particularly a promoter-primer, may be modified or blocked to prevent or inhibit initiation of DNA synthesis, as disclosed by Kacian et al., U.S. Pat. No. 5,554,516. The 3' end of the primer can be modified in a variety of ways well known in the art. By way of example, appropriate modifications to a promoter-primer can include the addition of ribonucleotides, 3' deoxynucleotide residues (e.g., cordycepin), 2',3'-dideoxynucleotide residues, modified nucleotides such as phosphorothioates, and non-nucleotide linkages such as those disclosed by Arnold et al. in U.S. Pat. No. 6,031,091 or alkane-diol modifications (see Wilk et al., "Backbone-Modified Oligonucleotides Containing a Butanediol-1,3 Moiety as a 'Vicarious Segment' for the Deoxyribosyl Moiety—Synthesis and Enzyme Studies," *Nucleic Acids Res.*, 18(8):2065 (1990)), or the modification may simply consist of a region 3' to the priming sequence that is non-complementary to the target nucleic acid sequence. Additionally, a mixture of different 3' blocked promoter-primers or of 3' blocked and unblocked promoter-primers may increase the efficiency of nucleic acid amplification, as described therein.

As disclosed above, the 5' end of primers may be modified to be resistant to the 5'-exonuclease activity present in some nucleic acid polymerases. Such modifications can be carried out by adding a non-nucleotide group to the terminal 5' nucleotide of the primer using techniques such as those disclosed by Arnold et al., U.S. Pat. No. 6,031,091.

Once synthesized, a selected oligonucleotide may be labeled by any well known method (see, e.g., Sambrook et al., supra, ch. 10). Useful labels include radioisotopes as well as non-radioactive reporting groups. Isotopic labels include $^3$H, $^{35}$S, $^{32}$P, $^{125}$I, $^{57}$Co, and $^{14}$C. Isotopic labels can be introduced into the oligonucleotide by techniques known in the art such as nick translation, end labeling, second strand synthesis, the use of reverse transcription, and by chemical methods. When using radiolabeled probes, hybridization can be detected by autoradiography, scintillation counting, or gamma counting. The detection method selected will depend upon the particular radioisotope used for labeling.

Non-isotopic materials can also be used for labeling and may be introduced internally into the nucleic acid sequence or at the end of the nucleic acid sequence. Modified nucleotides may be incorporated enzymatically or chemically. Chemical modifications of the probe may be performed during or after synthesis of the probe, for example, through the use of non-nucleotide linker groups as disclosed by Arnold et al., U.S. Pat. Nos. 5,585,481, 5,639,604, and 6,031,091. Non-isotopic labels include fluorescent molecules (individual labels or combinations of labels, such as the fluorescence resonance energy transfer (FRET) pairs disclosed by Tyagi et al., "Detectably Labeled Dual Conformation Oligonucleotide Probes," U.S. Pat. No. 5,925,517), chemiluminescent molecules, enzymes, cofactors, enzyme substrates, haptens, or other ligands.

In one embodiment, the detection probes of the present disclosure are labeled using a non-nucleotide linker with an acridinium ester. Acridinium ester labeling may be performed as disclosed by Arnold et al., "Acridinium Ester Labelling and Purification of Nucleotide Probes," U.S. Pat. No. 5,185,439, the contents of which are hereby incorporated by reference herein.

2. Amplification of *Trichomonas vaginalis* Ribosomal Nucleic Acid

The amplification oligonucleotides of the present disclosure are directed to 18S regions of ribosomal nucleic acid derived from *T. vaginalis*. These amplification oligonucleotides may flank, overlap, or be contained within at least one of the target sequences of a detection probe (or its complement) used to detect the presence of *T. vaginalis* in a nucleic acid amplification assay. As indicated above, the amplification oligonucleotides may also include non-complementary bases at their 5' ends comprising a promoter sequence able to bind a RNA polymerase and direct RNA transcription using the target nucleic acid as a template. A T7 promoter sequence, such as SEQ ID NO:54, may be used. Examples of amplification oligonucleotides are listed in Table

TABLE 1

*T. vaginalis* 18S amplification oligonucleotides

| SEQ ID NO. | Sequence |
| --- | --- |
| 45 | gctaacgagcgagattatcgcc |
| 46 | gcuaacgagcgagauuaucgcc |
| 47 | ggcgataatctcgctcgttagc |
| 48 | ggcgauaaucucgcucguuagc |
| 49 | ggcatcacggacctgttattgc |
| 50 | gcaauaacaggguccgugaugcc |
| 51 | ggcatcacggacctgttattgc |
| 52 | ggcaucacggaccuguuauugc |
| 53 | aatttaatacgactcactatagggagaggcatcacggacctgttattgc |

In one embodiment, a set of at least two amplification oligonucleotides for amplifying *T. vaginalis*-derived nucleic acid is provided which includes: (i) a first amplification oligonucleotide having a base sequence comprising, overlapping with, consisting essentially of, consisting of, substantially corresponding to, or contained within the base sequence of SEQ ID Nos. 45-48; and (ii) a second amplification oligonucleotide having a base sequence comprising, overlapping with, consisting essentially of, consisting of, substantially corresponding to, or contained within the base sequence of SEQ ID Nos. 49-52. The second amplification oligonucleotide may include a 5' promoter sequence (e.g., the T7 promoter sequence of SEQ ID NO:54) as shown in SEQ ID NO:53.

Amplification oligonucleotides of the present disclosure may have modifications, such as blocked 3' and/or 5' termini (as discussed above) or sequence additions including, but not limited to, a specific nucleotide sequence recognized by a RNA polymerase (e.g., a promoter sequence for T7, T3 or SP6 RNA polymerase), a sequence which enhances initiation or elongation of RNA transcription by a RNA polymerase, or a sequence which may provide for intra-molecular base pairing and encourage the formation of secondary or tertiary nucleic acid structures.

Amplification oligonucleotides are used in any suitable nucleic acid amplification procedure now known or later developed. Existing amplification procedures include the polymerase chain reaction (PCR), transcription-mediated amplification (TMA), nucleic acid sequence-based amplification (NASBA), self-sustained sequence replication (3SR), ligase chain reaction (LCR), strand displacement amplification (SDA), and Loop-Mediated Isothermal Amplification (LAMP), each of which is well known in the art. See, e.g., Mullis, "Process for Amplifying Nucleic Acid Sequences," U.S. Pat. No. 4,683,202; Erlich et al., "Kits for Amplifying and Detecting Nucleic Acid Sequences," U.S. Pat. No. 6,197,563; Walker et al., *Nucleic Acids Res.*, 20:1691-1696 (1992); Fahy et al., "Self-sustained Sequence Replication (3SR): An Isothermal Transcription-Based Amplification System Alternative to PCR," *PCR Methods and Applications*, 1:25-33 (1991); Kacian et al., U.S. Pat. No. 5,399,491; Kacian et al., "Nucleic Acid Sequence Amplification Methods," U.S. Pat. No. 5,480,784; Davey et al., "Nucleic Acid Amplification Process," U.S. Pat. No. 5,554,517; Birkenmeyer et al., "Amplification of Target Nucleic Acids Using Gap Filling Ligase Chain Reaction," U.S. Pat. No. 5,427,930; Marshall et al., "Amplification of RNA Sequences Using the Ligase Chain Reaction," U.S. Pat. No. 5,686,272; "Walker, Strand Displacement Amplification," U.S. Pat. No. 5,712,124; Notomi et al., "Process for Synthesizing Nucleic Acid," European Patent Application No. 1 020 534 A1; Dattagupta et al., "Isothermal Strand Displacement Amplification," U.S. Pat. No. 6,214,587; and Helen H. Lee et al., "Nucleic Acid Amplification Technologies: Application To Disease Diagnosis" (1997). (Each of the foregoing amplification references is hereby incorporated by reference herein.) Any other amplification procedure which meets the definition of "nucleic acid amplification" supra is also contemplated by the inventors.

In one embodiment, amplification oligonucleotides of the present disclosure are unlabeled. In another embodiment, amplification oligonucleotides of the present disclosure include one or more reporter groups to facilitate detection of a target nucleic acid in combination with or exclusive of a detection probe. A wide variety of methods are available to detect an amplified target sequence. For example, the nucleotide substrates or the amplification oligonucleotides can include a detectable label that is incorporated into newly synthesized DNA. The resulting labeled amplification product is then generally separated from the unused labeled nucleotides or amplification oligonucleotides and the label is detected in the separated product fraction. (See, e.g., Wu, "Detection of Amplified Nucleic Acid Using Secondary Capture Oligonucleotides and Test Kit," U.S. Pat. No. 5,387,510.)

A separation step is not required, however, if the amplification oligonucleotide is modified by, for example, linking it to an interacting label pair, such as two dyes which form a donor/acceptor dye pair. The modified amplification oligonucleotide can be designed so that the fluorescence of one dye pair member remains quenched by the other dye pair member, so long as the amplification oligonucleotide does not hybridize to target nucleic acid, thereby physically separating the two dyes. Moreover, the amplification oligonucleotide can be further modified to include a restriction endonuclease recognition site positioned between the two dyes so that when a hybrid is formed between the modified amplification oligonucleotide and target nucleic acid, the restriction endonuclease recognition site is rendered double-stranded and available for cleavage or nicking by an appropriate restriction endonuclease. Cleavage or nicking of the hybrid then separates the two dyes, resulting in a change in fluorescence due to decreased quenching which can be detected as an indication of the presence of the target organism in the test sample. This type of modified amplification oligonucleotide, referred to as a "signal primer," is disclosed by Nadeau et al., "Detection of Nucleic Acids by Fluorescence Quenching," U.S. Pat. No. 6,054,279.

Substances which can serve as useful detectable labels are well known in the art and include radioactive isotopes, fluorescent molecules, chemiluminescent molecules, chromophores, as well as ligands such as biotin and haptens which, while not directly detectable, can be readily detected by a reaction with labeled forms of their specific binding partners, e.g., avidin and antibodies, respectively.

Another approach is to detect the amplification product by hybridization with a detectably labeled oligonucleotide probe and measuring the resulting hybrids in any conventional manner. In particular, the product can be assayed by hybridizing a chemiluminescent acridinium ester-labeled oligonucleotide probe to the target sequence, selectively hydrolyzing the acridinium ester present on unhybridized probe, and measuring the chemiluminescence produced from the remaining acridinium ester in a luminometer. (See, e.g., Arnold et al., U.S. Pat. No. 5,283,174, and Norman C. Nelson et al., "Nonisotopic Probing, Blotting, and Sequencing," ch. 17 (Larry T. Kricka ed., 2d ed. 1995).)

Because genitourinary specimens tend to contain large amounts of *T. vaginalis* when an individual is infected with the organism, it may be desirable to include a co-amplifiable pseudo target in the amplification reaction mixture in order to render the assay less sensitive, especially when quantification is an objective of the assay. Pseudo targets and their uses are disclosed by Nunomura, "Polynucleotide Amplification Method," U.S. Pat. No. 6,294,338, the contents of which are hereby included by reference herein. In the present application, the pseudo target may be, for example, a known amount of a *Trichomonas tenax* 18S rRNA transcript that can be amplified with a set of amplification oligonucleotides of the present disclosure under amplification conditions, but which does not contain or result in a sequence that is detectable with a detection probe of the present disclosure. Alternatively a pseudo target may be a synthetic oligonucleotide that can be amplified with a set of amplification oligonucleotides of the present disclosure under amplification conditions, but which does not contain or result in a sequence that is detectable with a detection probe of the present disclosure.

D. Sample Processing

Sample processing prior to amplification or detection of a target sequence may be necessary or useful for discriminating a target sequence from non-target nucleic acid present in a sample. Sample processing procedures may include, for example, direct or indirect immobilization of nucleic acids and/or oligonucleotides from the liquid phase in a heterogeneous assay. With some procedures, such immobilization may require multiple hybridization events. Ranki et al., "Detection of Microbial Nucleic Acids by a One-Step Sandwich Hybridization Test," U.S. Pat. Nos. 4,486,539 and 4,563,419, for example, disclose a one-step nucleic acid "sandwich" hybridization method involving the use of a solid-phase bound nucleic acid having a target complementary sequence and a labeled nucleic acid probe which is complementary to a distinct region of the target nucleic acid. Stabinsky, "Methods and Kits for Performing Nucleic Acid Hybridization Assays," U.S. Pat. No. 4,751,177, discloses methods including a "mediator" polynucleotide that reportedly overcomes sensitivity problems associated with Ranki☐s method resulting from leakage of immobilized probe from the solid support. Instead of directly immobilizing the target nucleic acid, the mediator polynucleotides of Stabinsky are used to bind and indirectly immobilize target polynucleotide:probe polynucleotide complexes which have formed free in solution.

Any known solid support may be used for sample processing, such as matrices and particles free in solution. The solid support may be, for example, nitrocellulose, nylon, glass, polyacrylate, mixed polymers, polystyrene, silane polypropylene, or particles having a magnetic charge to facilitate recovering sample and/or removing unbound nucleic acids or other sample components. In one embodiment the supports are magnetic spheres that are monodisperse (i.e., uniform in size±5%), thereby providing consistent results, which is particularly advantageous for use in an automated procedure. One such automated procedure is disclosed by Ammann et al., "Automated Process for Isolating and Amplifying a Target Nucleic Acid Sequence," U.S. Pat. No. 6,335,166, the contents of which are incorporated by reference.

An oligonucleotide for immobilizing a target nucleic acid on a solid support may be joined directly or indirectly to the solid support by any linkage or interaction which is stable under assay conditions (e.g., conditions for amplification and/or detection). Referred to herein as an "immobilized probe," this oligonucleotide may bind directly to the target nucleic acid or it may include a base sequence region, such as a homopolymeric tract (e.g., a poly dT) or a simple short repeating sequence (e.g., an AT repeat), which hybridizes to a complementary base sequence region present on a capture probe. Direct joining occurs when the immobilized probe is joined to the solid support in the absence of an intermediate group. For example, direct joining may be via a covalent linkage, chelation or ionic interaction. Indirect joining occurs when the immobilized probe is joined to the solid support by one or more linkers. A "linker" is a means for binding at least two different molecules into a stable complex and contains one or more components of a binding partner set.

Members of a binding partner set are able to recognize and bind to each other. Binding partner sets may be, for example, receptor and ligand, enzyme and substrate, enzyme and cofactor, enzyme and coenzyme, antibody and antigen, sugar and lectin, biotin and streptavidin, ligand and chelating agent, nickel and histidine, substantially complementary oligonucleotides, and complementary homopolymeric nucleic acids or homopolymeric portions of polymeric nucleic acids. Components of a binding partner set are the regions of the members that participate in binding.

A sample processing system having practical advantages in terms of its ease of use and rapidity comprises an immobilized probe containing a base sequence which is complementary to a base sequence of a capture probe, referred to herein as an "immobilized probe binding region." The capture probe additionally contains a base sequence, referred to herein as a "target-complementary base sequence," which may specifically hybridize to a target sequence contained in a target nucleic acid under assay conditions. (While specificity of the target-complementary base sequence of the capture probe for a region of the target nucleic acid is desirable to minimize the number of non-target nucleic acids remaining from the sample after a separation step, it is not a requirement of the capture probes of the present disclosure if the capture probes are being used solely to isolate target nucleic acid.) If the capture probe is not being employed to isolate a target nucleic acid for subsequent amplification of a target sequence, the capture probe may further include a detectable label attached within or near the target-complementary base sequence, such as a substituted or unsubstituted acridinium ester. The labeled capture probe may be used in a homogeneous or semi-homogenous assay to specifically detect hybrid nucleic acids without detecting single-stranded nucleic acids, such as the capture probe. A homogenous assay which could be used with this system is the hybridization protection assay (HPA), which is discussed above in the section entitled "Hybridization Conditions and Probe Design." Following the HPA format, label associated with capture probes which have not hybridized to target nucleic acids would be hydrolyzed with the addition of a mild base, while label associated with capture probe:target hybrids would be protected from hydrolysis.

An advantage of this latter assay system is that only a single target-specific hybridization event (capture probe:target) is necessary for target detection, rather than multiple such events (e.g., capture probe:target and probe:target or probe: amplicon) which are required in other sample processing procedures described herein. Also, fewer oligonucleotides in an assay tend to make the assay faster and simpler to optimize, since the overall rate at which a target nucleic acid is captured and detected is limited by the slowest hybridizing oligonucleotide. While the target-complementary base sequence of a capture probe may be less specific in alternative assay systems, it must still be rare enough to avoid significant saturation of the capture probe with non-target nucleic acids. Thus, the requirement that two separate and specific target sequences be identified in these alternative systems could place constraints on the identification of an appropriate target. By contrast, only one such target sequence is needed when the capture probe simultaneously functions as the detection probe.

Whichever approach is adopted, the assay needs to include means for detecting the presence of the target nucleic acid in the test sample. A variety of means for detecting target nucleic acids are well known to those skilled in the art of nucleic acid detection, including means which do not require the presence of a detectable label. Other means includes using a detectable label. A labeled probe for detecting the presence of a target nucleic acid would have to include a base sequence which is substantially complementary and specifically hybridizes to a target sequence contained in the target nucleic acid. Once the probe stably binds to the target nucleic acid, and the resulting target:probe hybrid has been directly or indirectly immobilized, unbound probe can be washed away or inactivated and the remaining bound probe can be detected and/or measured.

Sample processing systems combine the elements of detection and nucleic acid amplification. These systems first directly or indirectly immobilize a target nucleic acid using a capture probe, the captured target nucleic acid is purified by removing inter alia cellular debris, non-target nucleic acid and amplification inhibitors from the sample-containing vessel, which is followed by amplification of a target sequence contained in the target nucleic acid. The amplified product, in one embodiment, is then detected in solution with a labeled probe. (The target nucleic acid may remain in the immobilized state during amplification or it may be eluted from the solid support prior to amplification using appropriate conditions, such as by first incubating at a temperature above the $T_m$ of the capture probe:target complex and/or the $T_m$ of the capture probe:immobilized probe complex.) One embodiment of this system is disclosed by Weisburg et al., "Two-Step Hybridization and Capture of a Polynucleotide," U.S. Pat. No. 6,110,678. In this system, the capture probe hybridizes to the target nucleic acid and an immobilized probe hybridizes to the capture probe:target complex under different hybridization conditions. Under a first set of hybridization conditions, hybridization of the capture probe to the target nucleic acid is favored over hybridization of the capture probe to the immobilized probe. Thus, under this first set of conditions, the capture probe is in solution rather than bound to a solid support, thereby maximizing the concentration of the free capture probe and utilizing favorable liquid phase kinetics for hybridization to the target nucleic acid. After the capture probe has had sufficient time to hybridize to the target nucleic acid, a second set of hybridization conditions is imposed permitting in the capture probe:target complex to hybridize to the immobilized probe, thereby isolating the target nucleic acid in the sample solution. The immobilized target nucleic acid may then be purified, and a target sequence present in the target nucleic acid may be amplified and detected. A purification procedure which includes one or more wash steps is generally desirable when working with crude samples (e.g., clinical samples) to prevent enzyme inhibition and/or nucleic acid degradation due to substances present in the sample.

One embodiment of an amplification method is the transcription-mediated amplification method disclosed by Kacian et al., "Nucleic Acid Sequence Amplification Methods," U.S. Pat. No. 5,480,789. In accord with this method, a promoter-primer having a 3' region complementary to a portion of the target and a 5' promoter region and a primer having the same nucleotide sequence as a portion of the target are contacted with a target RNA molecule. The primer and promoter-primer define the boundaries of the target region to be amplified, including both the sense present on the target molecule and its complement, and thus the length and sequence of the amplicon. In this embodiment, the amplification oligonucleotides and immobilized target RNA are contacted in the presence of effective amounts of Moloney murine leukemia virus-derived reverse transcriptase and T7 RNA polymerase, both ribonucleotide and deoxyribonucleotide triphosphates, and necessary salts and cofactors at 42° C. Under these conditions, nucleic acid amplification occurs, resulting predominantly in the production of RNA amplicons of a sense opposite to that of the target nucleic acid. These amplicons can then be detected in solution by, for example, using an acridinium ester-labeled hybridization assay probe of the same sense as the target nucleic acid, employing HPA, as disclosed by Arnold et al. in U.S. Pat. No. 5,283,174.

The 3' terminus of the immobilized probe and the capture probe are, in one embodiment, "capped" or blocked to prevent or inhibit their use as templates for nucleic acid polymerase activity. Capping may involve adding 3' deoxyribonucleotides (such as cordycepin), 3',2'-dideoxynucleotide residues, non-nucleotide linkers, such as those disclosed by Arnold et al. in U.S. Pat. No. 6,031,091, alkane-diol modifications, or non-complementary nucleotide residues at the 3' terminus.

Those skilled in the art will recognize that the above-described methodology is amenable, either as described or with obvious modifications, to various other amplification schemes, including, for example, the polymerase chain reaction (PCR), Qβ replicase-mediated amplification, self-sustained sequence replication (3SR), strand displacement amplification (SDA), nucleic acid sequence-based amplification (NASBA), loop-mediated isothermal amplification (LAMP), and the ligase chain reaction (LCR).

E. Capture Probes for Isolating *Trichomonas vaginalis* Ribosomal Nucleic Acid

Capture probes of the present disclosure are designed to bind to and isolate nucleic acid derived from the 18S ribosomal nucleic acid of *T. vaginalis* in the presence of non-target nucleic acid. As such, the capture probes, in one embodiment, include both a target-complementary base sequence and an immobilized probe binding region. The target-complementary base sequence of the capture probes includes a base sequence which hybridizes to a target sequence derived from 18S ribosomal nucleic acid from *T. vaginalis* under assay conditions. While not essential, the target-complementary base sequence, in one embodiment, exhibits specificity for the target sequence in the presence of non-target nucleic acid under assay conditions. The immobilized probe binding region has a base sequence which hybridizes to an immobilized probe comprising a polynucleotide, or a chimeric containing polynucleotide sequences, which is joined to a solid support present in the test sample, either directly or indirectly. The target-complementary base sequence and the immobilized probe binding region may be joined to each other directly or by means of, for example, a nucleotide base sequence, an abasic sequence or a non-nucleotide linker.

In another embodiment of the present disclosure, a capture probe is provided for extracting target nucleic acid derived from *T. vaginalis* present in a test sample. The base sequence of the capture probe consists of a target-complementary base sequence that is perfectly complementary to a target sequence contained within a target domain selected from the group consisting of SEQ ID Nos. 77, 78, 79, 80, or and RNA/DNA combination equivalent to any of the foregoing. The target-complementary base sequence of the capture probe includes the base sequence of SEQ ID Nos. 81, 82, 83, 81, or an RNA/DNA combination equivalent to any of the foregoing. The capture probe may also include at least one base sequence that is non-complementary to the *T. vaginalis* nucleic acid. In another embodiment, the capture probes contain a target-complementary base sequence having a base sequence selected from the group consisting of SEQ ID Nos. 55, 56, 57, 58, 85, 86, 87, 88, 90, 91, 92, 93, 95, 96, 97, 98, 100, 101, 102, 103, or an RNA/DNA combination equivalent to any of the foregoing. The immobilized probe binding region of these capture probes comprises a base sequence which hybridizes to an immobilized probe joined directly or indirectly to a solid support provided to the test sample under assay conditions. In one example, the immobilized probe binding region comprises a homopolymeric region (e.g., poly dA) located at the 3' end of the capture probe which is complementary to a homopolymeric region (e.g., poly dT) located at the 5' end of the immobilized probe. The immobilized probe binding region may consists of the base sequence of SEQ ID NO:60 tttaaaaaaaaaaaaaaaaaaaaaaaaaaaaa. Other base sequences may be incorporated into the immobilized probe binding region, including, for example, short repeating sequences.

To prevent undesirable cross-hybridization reactions, the capture probes of the present disclosure, in one embodiment, exclude nucleotide base sequences, other than the nucleotide base sequence of the target-complementary base sequence, which can stably bind to nucleic acid derived from any organism which may be present in the test sample under assay conditions. Consistent with this approach, and in order to maximize the immobilization of capture probe:target complexes which are formed, the nucleotide base sequence of the immobilized probe binding region is, in one embodiment, designed so that it can stably bind to a nucleotide base sequence present in the immobilized probe under assay conditions and not to nucleic acid derived from any organism which may be present in the test sample.

The target-complementary base sequence and the immobilized probe binding region of the capture probe may be selected so that the capture probe:target complex has a higher $T_m$ than the $T_m$ of the capture probe:immobilized probe complex. In this way, a first set of conditions may be imposed which favors hybridization of the capture probe to the target sequence, thereby providing for optimal liquid phase hybridization kinetics for hybridization of the capture probe to the target sequence. Once sufficient time has passed for the capture probe to bind to the target sequence, a second set of less stringent conditions may be imposed which allows for hybridization of the capture probe to the immobilized probe.

Capture probes of the present disclosure may also include a label or a pair of interacting labels for direct detection of the target sequence in a test sample. Non-limiting examples of labels, combinations of labels and means for labeling probes are set forth supra in the section entitled "Preparation of Oligonucleotides" and infra in the section entitled "Detection Probes to *Trichomonas vaginalis* Ribosomal Nucleic Acid." A particularly useful method for detecting the presence of a capture probe hybridized to a target nucleic acid is the Hybridization Protection Assay (HPA), which is described above in the section entitled "Hybridization Conditions and Probe Design." HPA is a homogenous assay which distinguishes between probe hybridized to target nucleic acid and probe which remains unhybridized. Signal detected from an HPA reaction vessel provides an indication of the presence or amount of target organisms in the test sample.

Despite their application in a direct detection assay, the most common use of capture probes is in the isolation and purification of target nucleic acid prior to amplifying a target sequence contained in the target nucleic acid. By isolating and purifying the target nucleic acid prior to amplification, the number of unintended amplification reactions (i.e., amplification of non-target nucleic acid) can be severely limited. And, to prevent or inhibit the capture probe itself from functioning as a template for nucleic acid polymerase activity in the presence of amplification reagents and under amplification conditions, the 3' end of the capture probe may be capped or blocked. Examples of capping agents include 3' deoxyribonucleotides, 3',2'-dideoxynucleotide residues, non-nucleotide linkers, alkane-diol modifications, and non-complementary nucleotide residues at the 3' terminus.

F. Detection Probes to *Trichomonas vaginalis* Ribosomal Nucleic Acid

This embodiment of the disclosure relates to novel detection probes. Hybridization is the association of two single strands of complementary nucleic acid to form a hydrogen-bonded double strand. A nucleic acid sequence able to hybridize to a nucleic acid sequence sought to be detected ("target sequence") can serve as a probe for the target sequence. Hybridization may occur between complementary nucleic acid strands, including DNA/DNA, DNA/RNA, and RNA/RNA, as well as between single-stranded nucleic acids wherein one or both strands of the resulting hybrid contain at least one modified nucleotide, nucleoside, nucleobase, and/or base-to-base linkage. In any case, two single strands of sufficient complementarity may hybridize to form a double-stranded structure in which the two strands are held together by hydrogen bonds between pairs of complementary bases. As described above, in general A is hydrogen-bonded to T or U, while G is hydrogen-bonded to C. At any point along the hybridized strands, therefore, the classical base pairs AT or AU, TA or UA, GC, or CG may be found. Thus, when a first single strand of nucleic acid contains sufficient contiguous complementary bases to a second, and those two strands are brought together under conditions that promote their hybridization, double-stranded nucleic acid will result. Accordingly, under appropriate conditions, double-stranded nucleic acid hybrids may be formed.

The rate and extent of hybridization is influenced by a number of factors. For instance, it is implicit that if one of the two strands is wholly or partially involved in a hybrid, it will be less able to participate in the formation of a new hybrid. By designing a probe so that a substantial portion of the sequence of interest is single-stranded, the rate and extent of hybridization may be greatly increased. Also, if the target is an integrated genomic sequence it will naturally occur in a double-stranded form, as is the case with a product of PCR. These double-stranded targets are naturally inhibitory to hybridization with a single-stranded probe and require denaturation (in at least the region to be targeted by the probe) prior to the hybridization step. In addition, there can be intra-molecular and inter-molecular hybrids formed within a probe if there is sufficient self-complementarity. Regions of the nucleic acid known or expected to form strong internal structures inhibitory to hybridization are less preferred. Examples of such structures include hairpin loops. Likewise, probes with extensive self-complementarity generally should be avoided. All these undesirable structures can be avoided through careful probe design, and commercial computer programs are available to search for these types of interactions, such as the Oligo Tech analysis software.

In some applications, probes exhibiting at least some degree of self-complementarity are desirable to facilitate detection of probe:target duplexes in a test sample without first requiring the removal of unhybridized probe prior to detection. Molecular torch probes are a type of self-complementary probes that are disclosed by Becker et al., "Molecular Torches," U.S. Pat. No. 6,361,945. The molecular torch probes disclosed Becker et al. have distinct regions of self-complementarity, referred to as "the target binding domain" and "the target closing domain," which are connected by a joining region and which hybridize to one another under predetermined hybridization assay conditions. When exposed to denaturing conditions, the complementary regions (which may be fully or partially complementary) of the molecular torch probe melt, leaving the target binding domain available for hybridization to a target sequence when the predetermined hybridization assay conditions are restored. And when exposed to strand displacement conditions, a portion of the target sequence binds to the target binding domain and displaces the target closing domain from the target binding domain. Molecular torch probes are designed so that the target binding domain favors hybridization to the target sequence over the target closing domain. The target binding domain and the target closing domain of a molecular torch probe include interacting labels (e.g., luminescent/quencher) positioned so that a different signal is produced when the molecular torch probe is self-hybridized as opposed to when the molecular torch probe is hybridized to a target nucleic acid, thereby permitting detection of probe:target duplexes in a test sample in the presence of unhybridized probe having a viable label or labels associated therewith.

Another example of detection probes having self-complementarity are the molecular beacon probes disclosed by Tyagi et al. in U.S. Pat. No. 5,925,517. Molecular beacon probes include nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open confirmation. The shift to the open confirmation is detectable due to reduced interaction of the label pair, which may be, for example, a fluorophore and quencher, such as DABCYL and EDANS.

The rate at which a probe hybridizes to its target is one measure of the thermal stability of the target secondary structure in the probe region. The standard measurement of hybridization rate is the $C_o t_{1/2}$, which is measured as moles of nucleotide per liter times seconds. Thus, it is the concentration of probe times the time at which 50% of maximal hybridization occurs at that concentration. This value is determined by hybridizing various amounts of probe to a constant amount of target for a fixed time. The $C_o t_{1/2}$ is found graphically by standard procedures. The probe:target hybrid melting temperature may be determined by isotopic methods well-known to those skilled in the art. The melting temperature ($T_m$) for a given hybrid will vary depending on the hybridization solution being used.

In one embodiment, detection probes are sufficiently complementary to the target nucleic acid sequence to hybridize therewith under stringent hybridization conditions. Examples of stringent conditions include a temperature of about 60° C. and a salt concentration of about 1.5 M. Examples of salts include, but are not limited to, lithium chloride, sodium chloride and sodium citrate.

Thus, in a first aspect, the present disclosure features detection probes able to distinguish *T. vaginalis*-derived nucleic acid from non-*T. vaginalis* nucleic acid (e.g., *Trichomonas tenax*) by virtue of the ability of the detection probe to preferentially hybridize to *T. vaginalis*-derived nucleic acid) under stringent hybridization conditions. Specifically, the detection probes contain an oligonucleotide having a base sequence that is substantially complementary to a target sequence present in *T. vaginalis*-derived nucleic acid.

In the case of a hybridization assay, the length of the target nucleic acid sequence and, accordingly, the length of the probe sequence can be important. In some cases, there may be several sequences from a particular region, varying in location and length, which will yield probes with the desired hybridization characteristics. In other cases, one sequence may have better hybridization characteristics than another that differs merely by a single base. While it is possible for nucleic acids that are not perfectly complementary to hybridize, the longest stretch of perfectly homologous base sequence will normally primarily determine hybrid stability. While probes of different lengths and base composition may be used, the probes in the present disclosure, are up to 100 bases in length in one embodiment, or are from 25 to 50 bases in length in another embodiment, or are from 25 to 35 bases in length in yet another embodiment.

The detection probes include a base sequence that is substantially complementary to a target sequence present in 18S ribosomal RNA (rRNA), or the encoding DNA (rDNA), of *T. vaginalis*. Thus, the detection probes are able to stably hybridize to a target sequence derived from *T. vaginalis* under stringent hybridization conditions. The detection probes may also have additional bases outside of the targeted nucleic acid region which may or may not be complementary to *T. vaginalis*-derived nucleic acid but which are not complementary to nucleic acid derived from a non-target organism which may be present in the test sample.

Probes (and amplification oligonucleotides) of the present disclosure may also be designed to include a capture tail comprised of a base sequence (distinct from the base sequence intended to hybridize to the target sequence) that can hybridize under predetermined hybridization conditions to a substantially complementary base sequence present in an immobilized oligonucleotide that is joined to a solid support. The immobilized oligonucleotide is, in one embodiment, joined to a magnetically charged particle that can be isolated in a reaction vessel during a purification step after a sufficient period of time has passed for probe to hybridize to target nucleic acid. (An example of an instrument which can be used to perform such a purification step is the DTS® 1600 Target Capture System (Gen-Probe; Cat. No. 5202).) The probe is, in one embodiment, designed so that the melting temperature of the probe:target hybrid is greater than the melting temperature of the probe:immobilized oligonucleotide hybrid. In this way, different sets of hybridization assay conditions can be employed to facilitate hybridization of the probe to the target nucleic acid prior to hybridization of the probe to the immobilized oligonucleotide, thereby maximizing the concentration of free probe and providing favorable liquid phase hybridization kinetics. This "two-step" target capture method is disclosed by Weisburg et al., "Two Step Hybridization and Capture of a Polynucleotide," U.S. Pat. No. 6,110,678, the contents of which are hereby incorporated by reference herein. Other target capture schemes which could be readily adapted to the present disclosure are well known in the art and include, for example, those disclosed by Ranki et al., "Detection of Microbial Nucleic Acids by a One-Step Sandwich Hybridization Test," U.S. Pat. No. 4,486,539, and Stabinsky, "Methods and Kits for Performing Nucleic Acid Hybridization Assays," U.S. Pat. No. 4,751,177.

For *T. vaginalis* detection probes, the terms "target nucleic acid sequence," "target nucleotide sequence," "target sequence," and "target region" all refer to a nucleic acid sequence present in *T. vaginalis* rRNA or rDNA, or a sequence complementary thereto, which is not identically present in the nucleic acid of a closely related species. Nucleic acids having nucleotide sequences complementary to a target sequence may be generated by target amplification techniques disclosed elsewhere herein.

Organisms closely related to *T. vaginalis* include *Trichomonas gallinae, Trichomonas tenax, Monotrichomonas* species ATCC No. 50693, *Ditrichomonas honigbergi, Tritrichomonas foetus, Tetratrichomonas gallinarum* and *Pentatrichomonas hominis*, with *Trichomonas tenax* being the most closely related. In addition to these organisms, organisms that might be expected to be present in a *T. vaginalis*-containing test sample include, for example, *Escherichia coli, Chlamydia trachomatis* and *Neiserria gonorrhoeae*. This list of organisms is by no means intended to be fully representative of the organisms that the *T. vaginalis* detection probes of the present disclosure can be used to distinguish over. In general, the *T. vaginalis* detection probes of the present disclosure can be used to distinguish *T. vaginalis*-derived nucleic acid from any non-*T. vaginalis* nucleic acid that does not stably hybridize with the probe(s) under stringent hybridization conditions. Examples of detection probes are listed in Table 2.

TABLE 2

*T. vaginalis* 18S Detection Probes

| SEQ ID NO. | Sequence |
|---|---|
| 1 | ttgccgaagtccttcggttaaagttctaattg |
| 2 | uugccgaaguccuucgguuaaaguucuaauug |
| 3 | caattagaactttaaccgaaggacttcggcaa |
| 4 | caauuagaacuuuaaccgaaggacuucggcaa |
| 5 | tgccgaagtccttcggttaaagttctaattgg |
| 6 | ugccgaaguccuucgguuaaaguucuaauugg |
| 7 | ccaattagaactttaaccgaaggacttcggca |
| 8 | ccaauuagaacuuuaaccgaaggacuucggca |

TABLE 2-continued

*T. vaginalis* 18S Detection Probes

| SEQ ID NO. | Sequence |
|---|---|
| 9 | gccgaagtccttcggttaaagttctaattggg |
| 10 | gccgaaguccuucgguuaaaguucuaauuggg |
| 11 | cccaattagaactttaaccgaaggacttcggc |
| 12 | cccaauuagaacuuuaaccgaaggacuucggc |
| 13 | ccgaagtccttcggttaaagttctaattggg |
| 14 | ccgaaguccuucgguuaaaguucuaauuggg |
| 15 | cccaattagaactttaaccgaaggacttcgg |
| 16 | cccaauuagaacuuuaaccgaaggacuucgg |
| 17 | cgaagtccttcggttaaagttctaattgggac |
| 18 | cgaaguccuucgguuaaaguucuaauugggac |
| 19 | gtcccaattagaactttaaccgaaggacttcg |
| 20 | gucccaauuagaacuuuaaccgaaggacuucg |
| 21 | cgaagtcittcggttaaagttctaattgggac |
| 22 | cgaaguciuucgguuaaaguucuaauugggac |
| 23 | gtcccaattagaactttaaccgaaigacttcg |
| 24 | gucccaauuagaacuuuaaccgaaigacuucg |
| 25 | gaaguccuucgguuaaagaucuaa |
| 26 | gaaguccuucgguuaaaguucuaa |
| 27 | ttagaactttaaccgaaggacttc |
| 28 | uuagaacuuuaaccgaaggacuuc |
| 29 | gtccttcggttaaagttctaattgg |
| 30 | guccuucgguuaaaguucaauugg |
| 31 | ccaattagaactttaaccgaaggac |
| 32 | ccaauuagaacuuuaaccgaaggac |
| 33 | ttcggttaaagttctaattgggactccctgcg |
| 34 | uucgguuaaaguucuaauugggacucccugcg |
| 35 | cgcagggagtcccaattagaactttaaccgaa |
| 36 | cgcagggagucccaauuagaacuuuaaccgaa |

In one embodiment, detection probes were designed around the 1150 base region of *T. vaginalis* 18S ribosomal RNA, GenBank accession number U17510.1 and GI number 687613. The *T. vaginalis* detection probes have a base sequence comprising, overlapping with, consisting essentially of, consisting of, substantially corresponding to, or contained within a base sequence of SEQ ID Nos. 1-36. The detection probes may include an acridinium ester label joined to the probes by means of a non-nucleotide linker positioned between nucleotides 6 and 7, 7 and 8, 10 and 11, 11 and 12, 13 and 14, 14 and 15, 15 and 16, 16 and 17, 17 and 18, 18 and 19, or 19 and 20. The acridinium ester label may be joined to the probe in accordance with the teachings of Arnold et al. in U.S. Pat. Nos. 5,185,439 and 6,031,091.

Once synthesized, the probes may be labeled with a detectable label or reporter group by any well-known method. (See, e.g., Sambrook et al., supra, ch. 10.) The probe may be labeled with a detectable moiety such as a radioisotope, antigen or chemiluminescent moiety to facilitate detection of the target sequence. Useful labels include radioisotopes as well as non-radioactive reporting groups. Isotopic labels include $^3$H, $^{35}$S, $^{32}$P, $^{125}$I, $^{57}$Co and $^{14}$C. Isotopic labels can be introduced into an oligonucleotide by techniques known in the art such as nick translation, end labeling, second strand synthesis, reverse transcription and by chemical methods. When using radiolabeled probes, hybridization can be detected by techniques such as autoradiography, scintillation counting or gamma counting. The chosen detection method depends on the particular radioisotope used for labeling.

Non-isotopic materials can also be used for labeling and may be introduced internally between nucleotides or at an end of the oligonucleotide. Modified nucleotides may be incorporated enzymatically or chemically. Chemical modifications of the oligonucleotide may be performed during or after synthesis of the oligonucleotide using techniques known in the art. For example, through use of non-nucleotide linker groups disclosed by Arnold et al. in U.S. Pat. No. 6,031,091. Non-isotopic labels include fluorescent molecules, chemiluminescent molecules, fluorescent chemiluminescent molecules, phosphorescent molecules, electrochemiluminescent molecules, chromophores, enzymes, enzyme cofactors, enzyme substrates, dyes and haptens or other ligands. Another useful labeling technique is a base sequence that is unable to stably hybridize to the target nucleic acid under stringent conditions. Probes of the present disclosure are, in one embodiment, labeled with an acridinium ester. (Acridinium ester labeling is disclosed by Arnold et al. in U.S. Pat. No. 5,185,439.)

The selected detection probe can then be brought into contact with a test sample suspected of containing *T. vaginalis*. Generally, the test sample is from a source that also contains unknown organisms. Typically, the source of the test sample will be a patient specimen, such as a genitourinary specimen. After bringing the probe into contact with nucleic acids derived from the test sample, the probe and sample-derived nucleic acids can be incubated under conditions permitting preferential hybridization of the probe to a target nucleic acid derived from *T. vaginalis* that may be present in the test sample in the presence of nucleic acid derived from other organisms present in the test sample.

After a detection probe has hybridized to target nucleic acid present in the test sample, the resulting hybrid may be separated and detected by various techniques well known in the art, such as hydroxyapatite adsorption and radioactive monitoring. Other techniques include those which involve selectively degrading label associated with unhybridized probe and then measuring the amount of remaining label associated with hybridized probe, as disclosed in U.S. Pat. No. 5,283,174. The inventors particularly prefer this latter technique.

EXAMPLES

Examples are provided below illustrating different aspects and embodiments of the disclosure. It is believed that these examples accurately reflect the details of experiments actually performed, however, it is possible that some minor discrepancies may exist between the work actually performed and the experimental details set forth below which do not affect the conclusion of these experiments. Skilled artisans will appreciate that these examples are not intended to limit the disclosure to the specific embodiments described therein.
Reagents Various reagents are identified in the examples below, the formulations and pH values (where relevant) of these reagents were as follows.

A "Lysis Buffer" contains 15 mM sodium phosphate monobasic monohydrate, 15 mM sodium phosphate dibasic anhydrous, 1.0 mM EDTA disodium dihydrate, 1.0 mM EGTA free acid, and 110 mM lithium lauryl sulfate, pH 6.7.

A "Urine Lysis Buffer" contains 150 mM HEPES free acid, 294 mM lithium lauryl sulfate, 57 mM lithium hydroxide monohydrate, 100 mM ammonium sulfate, pH 7.5.

A "Target Capture Reagent" contains 250 mM HEPES free acid dihydrate, 310 mM lithium hydroxide monohydrate, 1.88 M lithium chloride, 100 mM EDTA free acid, 2 M hydroxide to pH 6.4, and 250 µg/ml 1 micron magnetic particles Sera-Mag™ MG-CM Carboxylate Modified (Seradyn, Inc.; Indianapolis, Ind.; Cat. No. 24152105-050450) having oligo(dT)$_{14}$ covalently bound thereto.

A "Wash Solution" contains 10 mM HEPES free acid, 6.5 mM sodium hydroxide, 1 mM EDTA free acid, 0.3% (v/v) ethyl alcohol absolute, 0.02% (w/v) methyl paraben, 0.01% (w/v) propyl paraben, 150 mM sodium chloride, 0.1% (w/v) lauryl sulfate, sodium (SDS), and 4 M sodium hydroxide to pH 7.5.

An "Amplification Reagent" is a lyophilized form of a 3.6 mL solution containing 26.7 mM rATP, 5.0 mM rCTP, 33.3 mM rGTP and 5.0 mM rUTP, 125 mM HEPES free acid, 8% (w/v) trehalose dihydrate, 1.33 mM dATP, 1.33 mM dCTP, 1.33 mM dGTP, 1.33 mM dTTP, and 4 M sodium hydroxide to pH 7.5. The Amplification Reagent is reconstituted in 9.7 mL of "Amplification Reagent Reconstitution Solution" described below.

An "Amplification Reagent Reconstitution Solution" contains 0.4% (v/v) ethyl alcohol absolute, 0.10% (w/v) methyl paraben, 0.02% (w/v) propyl paraben, 33 mM KCl, 30.6 mM MgCl$_2$, 0.003% phenol red.

A "Primer Reagent" contains 1 mM EDTA disodium dihydrate, ACS, 10 mM Trizma☐ base, and 6M hydrochloric acid to pH 7.5.

An "Enzyme Reagent" is a lyophilized form of a 1.45 mL solution containing 20 mM HEPES free acid dihydrate, 125 mM N-acetyl-L-cysteine, 0.1 mM EDTA disodium dihydrate, 0.2% (v/v) TRITON X-100 detergent, 0.2 M trehalose dihydrate, 0.90 RTU/mL Moloney murine leukemia virus ("MMLV") reverse transcriptase, 0.20 U/mL T7 RNA polymerase, and 4M sodium hydroxide to pH 7.0. (One "unit" or "RTU" of activity is defined as the synthesis and release of 5.75 fmol cDNA in 15 minutes at 37° C. for MMLV reverse transcriptase, and for T7 RNA polymerase, one "unit" or "U" of activity is defined as the production of 5.0 fmol RNA transcript in 20 minutes at 37° C.) The Enzyme Reagent is reconstituted in 3.6 mL of "Enzyme Reagent Reconstitution Solution" described below.

An "Enzyme Reagent Reconstitution Solution" contains 50 mM HEPES free acid, 1 mM EDTA free acid, 10% (v/v) TRITON X-100 detergent, 120 mM potassium chloride, 20% (v/v) glycerol anhydrous, and 4 M sodium hydroxide to pH 7.0.

A "Probe Reagent" is a lyophilized form of a 3.6 mL solution containing 110 mM lithium lauryl sulfate, 10 mM of mercaptoethane sulfonic acid, 100 mM lithium succinate, and 3% PVP. The Probe Reagent is reconstituted in 36 mL of "Probe Reagent Reconstitution Solution" described below.

A "Probe Reagent Reconstitution Solution" contains 100 mM succinic acid, 73 mM lithium lauryl sulfate, 100 mM lithium hydroxide monohydrate, 15 mM aldrithiol, 1.2 M lithium chloride, 20 mM EDTA, 3% (v/v) ethyl alcohol, and 2M lithium hydroxide to pH 4.7.

A "Selection Reagent" contains 600 mM boric acid, ACS, 182.5 mM sodium hydroxide, ACS, 1% (v/v) TRITON X-100 detergent, and 4 M sodium hydroxide to pH 8.5.

A "Detection Reagents" comprises Detect Reagent I, which contains 1 mM nitric acid and 32 mM hydrogen peroxide, 30% (v/v), and Detect Reagent II, which contains 1.5 M sodium hydroxide.

An "Oil Reagent" is a silicone oil.

Oligonucleotide Synthesis

The oligonucleotides used in the following examples were synthesized using standard phosphoramidite chemistry, in accordance with the teachings of Caruthers et al, *Methods Enzymol.*, 154:287 (1987). The detection probe sequences were labeled with a 2-methoxyl acridinium ester, 9[[4-[3-[(2, 5-dioxo-1-pyrrolidinyl)oxy]-3-oxopropyl]phenoxy]carbonyl]-2, 10-dimethyl-acridinium trifluoromethane sulfonate, using the labeling method disclosed in Arnold, et al., U.S. Pat. No. 5,185,439. The acridinium ester (AE) was incorporated into the detection probe sequence via a non-nucleotide linker in accordance with the teachings of Arnold, et al., U.S. Pat. Nos. 5,585,481, 5,639,604, and 6,031,091, the contents of which are hereby incorporated by reference herein.

In Vitro Transcript

Unless otherwise indicated, the oligonucleotides in the following Examples were evaluated using purified in vitro transcript (IVT). The IVT was made by cloning a portion of the *T. vaginalis* 18S ribosomal RNA into a vector and then using the vector to transform cells. Briefly, total RNA from *T. vaginalis* strains ATCC No. 30488 and ATCC No. 30001 was amplified by reverse transcription polymerase chain reaction (RT-PCR) using amplification oligonucleotides having the base sequences of SEQ ID Nos. 69, 70, 73, and 74 which target a region of the 18S rRNA. The RT-PCR amplicons produced were initially cloned using pGEM®-T Easy Vector System II (Promega; Madison, Wis.; Cat. No. A1380). The cloned sequences were excised from the pGEM-T Easy vectors and recloned into pBluescript® II SK (+) vectors (Stratagene; La Jolla, Calif.; Cat. No, 212205) using restriction enzymes ApaI and Sac I. The pBluescript vectors were used to transform XL1 Blue Supercompentant Cells (Stratagene; Cat. No. 200236).

Example 1

Signal-to-Noise Ratios for Detection Probes Targeting the 1150 Region of *T. vaginalis* 18S rRNA In this example the light off kinetics for several AE-labeled detection probes were evaluated. Oligonucleotides having the base sequences of SEQ ID Nos. 75 and 76 were synthesized using 2'-O-Methyl RNA bases, all other oligonucleotides were synthesized using DNA. For each AE-labeled detection probe, the target sequence and linker position are indicated in Table 3 below. The "linker position" identifies the bases between which the linker is incorporated in the probe sequence. A probe having the nucleotide sequence of SEQ ID NO:9 was disclosed in Weisburg, et al., U.S. Pat. No. 7,381, 811.

TABLE 3

1150 Region Probe Sequences and Linker Positions

| Probe | SEQ ID NO. | Probe Sequence | Linker Position |
|---|---|---|---|
| A | 1 | ttgccgaagtccttcggttaaagttctaattg | 17/18 |
| B | 1 | ttgccgaagtccttcggttaaagttctaattg | 18/19 |
| C | 1 | ttgccgaagtccttcggttaaagttctaattg | 19/20 |
| D | 5 | tgccgaagtccttcggttaaagttctaattgg | 16/17 |
| E | 5 | tgccgaagtccttcggttaaagttctaattgg | 17/18 |
| F | 5 | tgccgaagtccttcggttaaagttctaattgg | 18/19 |
| G | 9 | gccgaagtccttcggttaaagttctaattggg | 15/16 |
| H | 9 | gccgaagtccttcggttaaagttctaattggg | 16/17 |
| I | 9 | gccgaagtccttcggttaaagttctaattggg | 17/18 |
| J | 13 | ccgaagtccttcggttaaagttctaattggg | 14/15 |
| K | 17 | cgaagtccttcggttaaagttctaattgggac | 13/14 |
| L | 17 | cgaagtccttcggttaaagttctaattgggac | 14/15 |
| M | 17 | cgaagtccttcggttaaagttctaattgggac | 15/16 |
| N | 75 | gaaguccuucgguuaaaguucuaa | 8/9 |
| O | 75 | gaaguccuucgguuaaaguucuaa | 13/14 |
| P | 75 | gaaguccuucgguuaaaguucuaa | 14/15 |
| Q | 76 | guccuucgguuaaaguucuaauugg | 10/11 |
| R | 76 | guccuucgguuaaaguucuaauugg | 11/12 |
| S | 76 | guccuucgguuaaaguucuaauugg | 16/17 |
| T | 33 | ttcggttaaagttctaattgggactccctgcg | 6/7 |
| U | 33 | ttcggttaaagttctaattgggactccctgcg | 7/8 |

The detection probes were tested to determine their signal-to-noise ratio using the Hybridization Protection Assay (HPA), in accordance with the teachings of Arnold et al., U.S. Pat. No. 5,283,174. Briefly, each labeled probe was diluted to 1.05e6 relative light units (RLU) per 100 microliters (μL) of Probe Reagent and 100 μL of the diluted labeled probe were added to a 12 millimeter (mm)×75 mm tube. Reconstituted Amplification Reagent (75 μL) with or without 0.5 picomoles (pmol) of probe complement (SEQ ID NO:62 for all probe sequences except SEQ ID NO:33, which used SEQ ID NO:63) was added to the appropriate tubes. Enzyme Reagent (25 μL) was also added to each tube. Oil Reagent (200 μL) was added to prevent evaporation and the tubes were incubated for 20 minutes at 62° C. to allow the labeled probes to hybridize to the probe complement, if present. Label associated with non-hybridized probes was inactivated by adding 250 μL of Selection Reagent and incubating at 62° C. for 10 minutes. The tubes were cooled to room temperature for 15 minutes. The tubes were analyzed in a LEADER luminometer (Gen-Probe Incorporated; San Diego, Calif.) that was capable of automatically injecting 200 μL, of Detect Reagent I followed by 200 μL of Detect Reagent II, and then repeatedly reading emission light in the tubes for a specified period of time. For all probes except Probe T and Probe U, five replicates were run with the probe complement (SEQ ID NO:62) and five replicates were run without the probe complement. For Probe T and Probe U, ten replicates were run with the probe complement (SEQ ID NO:63) and ten replicates were run without the probe complement. The results were measured in RLU. The signal-to-noise ratios for the detection probes were compared to signal-to-noise ratios for the control sample and control probe, both of which used non-*T. vaginalis* target sequences. The detection probes were tested in four different batches and a control sample and control probe were run with each batch. The control sample and control probe used in each batch contained the same non-*T. vaginalis* target sequence. Probes A, B, C, and I were tested in batch 1; Probes D, E, F, G, H, I, K, L, and M were tested in batch 2; Probes N, O, P, Q, R, and S were tested in batch 3; and Probes T and U were tested in batch 4. The results are summarized in Table 4 below and indicate that Probes B, G, K, L, M, N, and T had signal-to-noise ratios that were comparable or better than the control. The coefficient of variance (CV) is expressed as a percentage.

TABLE 4

Signal to Noise Ratio Results

| Detection Probe | Negative Ave. RLU | % CV | Positive Ave. RLU | % CV | Signal-to-Noise Ratio |
|---|---|---|---|---|---|
| Control | 6,679 | 48 | 1,662,158 | 2 | 249 |
| A | 25,583 | 4 | 534,363 | 2 | 21 |
| B | 2,019 | 5 | 636,015 | 1 | 315 |
| C | 3,433 | 27 | 615,569 | 3 | 179 |
| J | 35,634 | 5 | 669,623 | 3 | 19 |
| Control | 2,686 | 4 | 1,115,418 | 2 | 415 |
| D | 21,934 | 11 | 723,867 | 4 | 33 |
| E | 2,475 | 26 | 772345 | 4 | 312 |
| F | 2,370 | 18 | 632,216 | 6 | 267 |
| G | 2,136 | 16 | 827,947 | 3 | 388 |
| H | 3,024 | 22 | 704,997 | 2 | 233 |
| I | 4,066 | 25 | 882,684 | 3 | 217 |
| K | 1,688 | 12 | 854,857 | 4 | 507 |
| L | 2,194 | 14 | 1,034,094 | 5 | 471 |
| M | 2,136 | 16 | 827,947 | 3 | 388 |
| Control | 3,550 | 24 | 1,069,428 | 5 | 301 |
| N | 3,406 | 3 | 1,083,026 | 8 | 318 |
| O | 1,104 | 8 | 9,507 | 6 | 9 |
| P | 1,997 | 4 | 178,286 | 14 | 89 |
| Q | 4,381 | 7 | 53,409 | 3 | 12 |
| R | 1,856 | 3 | 47,700 | 5 | 26 |
| S | 2,189 | 3 | 14,000 | 4 | 6 |
| Control* | 4,163 | 8 | 1,577,309 | 1 | 378 |
| T* | 865 | 7 | 936,304 | 1 | 1,082 |
| U* | 11,134** | 181** | 970,856 | 3 | 87** |
|  | 1,085*** | 14*** |  |  | 895*** |

*ten replicates run
**2 out of 10 replicates had extra enzyme added due to a mechanical error
***Statistics were recalculated without the two outliers Example 2

Cross-Reactivity of Probes Targeting the 1150 Region of *T. vaginalis* 18S rRNA with *Trichomonas tenax*

In this example, the specificity of several detection probes evaluated in Example 1 were further evaluated to determine their cross-reactivity with *Trichomonas tenax*, which is the most closely related protozoa to *T. vaginalis* and therefore most likely to cross-react with the *T. vaginalis* probes. The AE incorporation site for each detection probe was the same as those listed in Table 3 above. The detection probes were evaluated using the same method described in Example 1 with one modification, the probe complement in the Amplification Reagent was replaced with 0.5 pmol of *T. tenax* in vitro transcript (IVT). *Trichomonas tenax* IVT was made by amplifying total RNA from *T. tenax* cells (ATCC No. 30207) using RT-PCR with SEQ ID Nos. 69 and 74. The RT-PCR amplicons were cloned into pCR-Script® Amp SK(+) vectors (Stratagene). The vectors were used to transform XL10-Gold® Ultracompetent Cells (Stratagene). For each probe, five replicates were run with *T. tenax* IVT and five replicates were run without *T. tenax* IVT. The detection probes were compared to the same control probe sequence and control sample that was used in Example 1. The detection probes were tested in two different batches and the control was run for each batch. Probes K and L were tested in batch 1 and Probes N, O, P, Q, R, and S tested in batch 2. The results are summarized in Table 5 below and indicate that the detection probes tested in this experiment did not cross-react with the *T. tenax* IVT.

TABLE 5

Cross-Reactivity With *T. tenax*

| Detection Probe | Negative Ave. RLU | % CV | Positive Ave. RLU | % CV | Signal-to-Noise Ratio |
|---|---|---|---|---|---|
| Control | 1,177 | 18 | 963,684 | 1 | 819 |
| K | 831 | 5 | 1,074 | 13 | 1 |
| L | 771 | 5 | 983 | 2 | 1 |
| Control | 4,960 | 23 | 1,199,459 | 5 | 242 |
| N | 660 | 5 | 7,914 | 4 | 12 |
| O | 969 | 17 | 1,276 | 8 | 1 |
| P | 610 | 4 | 2,063 | 5 | 3 |
| Q | 756 | 4 | 20,040 | 1 | 27 |
| R | 761 | 4 | 7,899 | 6 | 10 |
| S | 852 | 2 | 7,427 | 2 | 9 |

Example 3

Detection of In Vitro Transcripts Derived from Two Strains of *T. vaginalis* with *T. vaginalis* Detection Probe In this example, Probe L (SEQ ID NO:17, AE incorporated using a linker positioned between bases 14 and 15) was evaluated to determine its ability to detect two *T. vaginalis* strains, ATCC Nos. 30488 and 30001. Probe L was combined with a target capture probe (SEQ ID NO:59) and amplification oligonucleotides (SEQ ID Nos. 45, 53, and 61). SEQ ID Nos. 59, 45, and 53 are disclosed in Weisburg, et al., U.S. Pat. No. 7,381,811. Probe L was evaluated using: (1) Target Capture, described in Weisburg et al., U.S. Pat. No. 6,110,678; (2) Transcription-Mediated Amplification (TMA), described in Kacian et al. in U.S. Pat. Nos. 5,399,491 and 5,480,784 (the contents of which are incorporated by reference) and by Lee et al., supra, ch. 8; and (3) Hybridization Protection Assay (HPA), described in Arnold et al., U.S. Pat. No. 5,283,174. The protocols for each method are briefly described below.

IVT derived from these strains and stored in Lysis Buffer were diluted with Lysis Buffer to 100e6, 75e6, 50e6, 25e6, 10e6 and 0 copies per milliliter (mL) and 400 μL of each concentration were placed in separate 12 mm×75 mm tubes. Target Capture Reagent, 100 μL containing 1 nanomole (nmol) per liter (L) of SEQ ID NO:59, was added to each tube and the tubes were covered and incubated at 62° C. for 30 minutes to immobilize the IVT, if present, on the magnetic beads. The magnetic beads were pelleted using a DTS® 400

Target Capture System (Gen-Probe; Cat. No. 104555) and the supernatant was aspirated. The magnetic beads were resuspended in 1 mL of Wash Solution, re-pelleted and the Wash Solution was aspirated. The magnetic beads were resuspended in 75 µL of reconstituted Amplification Reagent containing 53 pmol/mL of SEQ ID NO:45; 53 pmol/mL of SEQ ID Nos. 53; and 4.4 pmol/L of SEQ ID NO:61. Oil Reagent (200 µL) was added to prevent evaporation and the tubes were covered and incubated at 62° C. for 10 minutes to disrupt secondary structures of the transcripts and allow the primer to bind. The tubes were then incubated at 42° C. for 5 minutes bring them to the appropriate temperature for the enzymes. Reconstituted Enzyme Reagent (25 µL) was added and the tubes were incubated at 42° C. for 60 minutes to allow the enzymes to amplify the target nucleic acid. Probe Reagent (100 µL) containing 2e6 RLU of Probe L was added to each tube. The tubes were briefly vortexed, covered, and incubated at 62° C. for 20 minutes to allow the probe to hybridize to the amplified nucleic acid. The tubes were incubated at room temperature for 5 minutes. Label on the non-hybridized probes was inactivated by adding 250 µl, of Selection Reagent and incubating at 62° C. for 10 minutes. The tubes were cooled at room temperature for 15 minutes. The tubes were analyzed in a LEADER luminometer capable of automatically injecting 200 µL of Detect Reagent I, followed by 200 µL of Detect Reagent II, and then repeatedly reading the emission light in the tubes. Five replicates were run for each IVT concentration. The results were measured in RLU and a minimum of 100,000 RLU was the threshold for a test to be considered positive. The results are summarized in Table 6 below and indicate that Probe L performed very differently between the two T. vaginalis strains. For the ATCC No. 30001 strain, Probe L detected every concentration at over 1 million RLU. For the ATCC No. 30488 strain, Probe L showed a gradient effect correlating with the concentration of IVT. Plus, the RLU at the highest concentration of ATCC No. 30488 was roughly half of the RLU at the lowest concentration of ATCC No. 3011. This suggests that Probe L is not as sensitive at detecting the ATCC No. 30488 strain as it is at detecting the ATCC No. 30001 strain.

TABLE 6

Detection of T. vaginalis Strains Using Probe L

| IVT | ATCC No. 30001 | | ATCC No. 30488 | |
|---|---|---|---|---|
| Amt. | Ave. RLU | % CV | Ave. RLU | % CV |
| 0 | 3,665 | 8 | 1,693 | 5 |
| 10e6 | 1,465,270 | 3 | 127,006 | 9 |
| 25e6 | 1,468,481 | 3 | 212,967 | 21 |
| 50e6 | 1,487,129 | 2 | 464,798 | 7 |
| 75e6 | 1,393,655 | 2 | 490,382 | 13 |
| 100e6 | 1,198,562 | 4 | 714,740 | 7 |

Example 4

Detection of In Vitro Transcripts Derived from Two Strains of T. vaginalis with T. vaginalis Detection Probe In this example, Probe T (SEQ ID NO:33, AE incorporated using a linker positioned between bases 6 and 7) was evaluated to determine its ability to detect two T. vaginalis strains, ATCC No. 30488 and ATCC No. 30001. Probe T was combined with three amplification oligonucleotides (SEQ ID Nos. 45, 53, and 61) and evaluated using TMA and HPA. IVT derived from these strains and stored in Lysis Buffer were diluted with reconstituted Amplification Reagent to 140e6, 10e6, 1e6 and 0 copies per 187.5 µL. The diluted IVT (75 µL) was added to individual 12 mm×75 min tubes. Amplification oligonucleotides were added to each tube for a final concentration of 53 pmol/mL of SEQ ID NO:45; 53 pmol/mL of SEQ ID Nos. 53; and 4.4 pmol/L of SEQ ID NO:61 in 75 µL. Oil Reagent (200 µL) was added to each tube, the tubes were covered and incubated at 62° C. for 10 minutes. Reconstituted Enzyme Reagent (25 µL) was added and the tubes were incubated at 42° C. for 60 minutes. Probe Reagent (100 µL) containing 2e6 RLU of Probe T was added to each tube and the tubes were incubated at 62° C. for 20 minutes followed by 5 minutes at room temperature. Label on the non-hybridized probes was inactivated by adding 250 µL of Selection Reagent and incubating at 62° C. for 10 minutes. The tubes were cooled at room temperature for 15 minutes. The tubes were analyzed in a LEADER luminometer. Ten replicates were run for each IVT concentration. The results are summarized in Table 7 below and the RLU values of this table indicate that Probe T was able to detect both of the T. vaginalis strains with similar sensitivity.

TABLE 7

Detection of T. vaginalis Strains Using Probe T

| IVT | ATCC No. 30001 | | ATCC No. 30488 | |
|---|---|---|---|---|
| Amt. | Ave. RLU | % CV | Ave. RLU | % CV |
| 0 | 1,491 | 7 | 1,491 | 7 |
| 1e6 | 1,293,237 | 3 | 1,399,276 | 3 |
| 10e6 | 1,425,110 | 1 | 1,447,286 | 3 |
| 140e6 | 1,344,732 | 4 | 1,498,959 | 7 |

Example 5

Cross-Reactivity of T. vaginalis Detection Probe with Pentatrichomonas hominis and Trichomonas tenax In this example, Probe T (SEQ ID NO:33, AE incorporated using a linker positioned between bases 6 and 7) was evaluated to determine its cross-reactivity with Pentatrichomonas hominis (ATCC No. 30000) and Trichomonas tenax (ATCC No. 30207), two bacteria that are closely related to T. vaginalis. Probe T was evaluated at 2e6 RLU per 100 µL using Target Capture, TMA and HPA. The procedures and concentrations were the same as those described in Example 3, unless otherwise indicated. The target capture probe was SEQ ID NO:59 and the amplification oligonucleotides were SEQ ID Nos. 45, 53, and 61. Pentatrichomonas hominis was tested at 9.6e5 cells per test and T. tenax was tested at 3.8e5 cells per test. Twenty replicates were run for each microorganism. Trichomonas vaginalis in vitro transcript at 1e6 copies per test was used as the positive control and Lysis Buffer was used as the negative control, ten replicates were run for each control. The results are summarized in Table 8 below and indicate that Probe T does not cross-react with P. hominis or T. tenax.

TABLE 8

Cross-Reactivity of Probe T

| | Ave. RLU | % CV |
|---|---|---|
| Neg. control | 1,197 | 8 |
| Pos. control | 929,906 | 3 |

TABLE 8-continued

Cross-Reactivity of Probe T

| | Ave. RLU | % CV |
|---|---|---|
| P. hominis | 6,424 | 16 |
| T. tenax | 3,829 | 21 |

Example 6

Sensitivity of T. vaginalis Detection Probe

In this example, the sensitivity of Probe T, (SEQ ID NO:33, AE incorporated using a linker positioned between bases 6 and 7) was evaluated using 0, 1e-7, 1e-6, 1e-5, 1e-4, 0.001, 0.01, and 1 cell equivalents of T. vaginalis lysate. Probe T was evaluated at 2.5e6 RLU per 100 µL of Probe Reagent. Probe T was evaluated using Target Capture, TMA, and HPA. The procedures and concentrations were the same as those described in Example 3, unless otherwise indicated. The capture probe had the nucleotide sequence of SEQ ID NO:59 and the amplification oligonucleotides had the nucleotide sequences of SEQ ID Nos. 45, 53, and 61. Ten replicates were run for each cell concentration. The results are summarized in Table 9 below and indicate that the oligonucleotide combination of SEQ ID Nos. 59, 45, 53, 61, and Probe T was able to detect the equivalent of 0.01 T. vaginalis cells.

TABLE 9

Sensitivity of the T. vaginalis Probe T

| T. vaginalis Cell Equivalents | Ave. RLU | % CV |
|---|---|---|
| 0 | 1,500.9 | 2 |
| 1e-7 | 1,330.9 | 3 |
| 1e-6 | 1,414.0 | 7 |
| 1e-5 | 2,160.9 | 19 |
| 1e-4 | 7,067.2 | 19 |
| 0.001 | 58,824.7 | 10 |
| 0.01 | 452,465.1 | 15 |
| 0.1 | 1,374,721 | 3 |
| 1 | 1,458,061 | 2 |

Example 7

Cross-Reactivity of T. vaginalis Detection Probe with Common Genitourinary Bacteria In this example, the specificity of Probe T (SEQ ID NO:33, AE incorporated using a linker positioned between bases 6 and 7), combined with a target capture probe (SEQ ID NO:59) and amplification oligonucleotides (SEQ ID Nos. 45, 53, and 61), was evaluated against several common urogenital bacteria. The bacteria tested were the following: Chlamydia trachomatis, Neiserria gonorrhoeae, Mycoplasma genitalium (ATCC No. 33530), Derxia gummosa (ATCC No. 15994), Enterococcus faecalis (ATCC No. 19433), Moraxella osloensis, Neiserria meningitidis (serogroups A (ATCC No. 13077), B (ATCC No. 23255), C (ATCC No. 13109), and D (ATCC No. 13113)), Lactobacillis acidophilus (ATCC No. 4356), Lactobacillis brevis (ATCC No. 14869), Lactobacillis jensonii (ATCC No. 25258), Lactobacillis lactis (ATCC No. 11454), Candida albicans (ATCC No. 18804), Candida glabrata (ATCC No. 48435), Candida parapsilosis (ATCC No. 22019), Candida tropicalis (ATCC No. 750), Escherichia coli (ATCC No. 25922), Gardenerella vaginalis (ATCC No. 14018), Staphylococcus aureus (ATCC No. 12598), Staphylococcus eppidermidis (ATCC No. 14990), Giardia intestinalis (ATCC No. 30888), and Ureaplasma urealyticum (ATCC No. 27618).

For each bacteria listed above, approximately 1e6 bacteria were lysed in 400 µL of Lysis Buffer in a 12 mm×75 mm test tube. Target Capture Reagent (100 µL) containing 1 mmol/L of SEQ ID NO:59 was added to each tube and the tubes were incubated at 62° C. for 30 minutes. The tubes were then incubated for 30 minutes at room temperature. The magnetic beads in the Target Capture Reagent were pelleted using a magnet separation unit and the supernatant was aspirated. The magnetic beads were resuspended in 1 mL of Wash Solution, re-pelletted and the Wash Solution was aspirated. The magnetic beads were resuspended in 75 µL of reconstituted Amplification Reagent containing 53 pmol/mL of SEQ ID NO:45; 53 pmol/mL of SEQ ID Nos. 53; and 0.4.4 pmol/L of SEQ ID NO:61. Oil Reagent (200 µL) was added to each tube and the tubes were incubated at 62° C. for 10 minutes. The tubes were then incubated at 42° C. for 5 minutes. Reconstituted Enzyme Reagent (25 µL) was added to each tube and the tubes were incubated at 42° C. for 60 minutes. Reconstituted Probe Reagent (100 µL) containing 2e6 RLU of Probe T was added to each tube and the tubes were incubated at 62° C. for 20 minutes followed by a 5 minute room temperature incubation. Selection Reagent (250 µL) was added to each tube and the tubes were incubated at 62° C. for 10 minutes. The tubes were then cooled at room temperature for 15 minutes. The tubes were analyzed in a LEADER luminometer that automatically added Detect Reagent I (200 µL) and Detect Reagent II (200 µL) and repeatedly read the light emission form the tubes. The negative control did not have any bacteria or T. vaginalis in vitro transcript, the positive control had 1e6 copies of T. vaginalis in vitro transcript. The controls were run in duplicate, whereas the bacteria were run in triplicate. The results are listed in Table 10 below and indicate that Probe T did not cross-react with the common urogential bacteria.

TABLE 10

Cross-Reactivity Against Genitourinary Bacteria Results

| Bacteria | Ave. RLU | % CV |
|---|---|---|
| Neg. Control | 2,004 | 4 |
| Pos. Control | 2,247,270 | 1 |
| C. trachomatis | 1,859 | 3 |
| N. gonorrhoeae | 1,746 | 3 |
| M. genitalium | 1,664 | 5 |
| D. gummosa | 1,784 | 6 |
| E. faecalis | 1,706 | 3 |
| M. osloensis | 1,644 | 5 |
| N. meningitidis, Strain A | 1,715 | 2 |
| N. meningitidis, Strain B | 1,672 | 0 |
| N. meningitidis, Strain C | 1,621 | 20 |
| N. meningitidis, Strain D | 1,805 | 24 |
| L. acidophilus | 2,515 | 5 |
| L. brevis | 1,753 | 0 |
| L. jensonii | 1,618 | 5 |
| L. lactis | 1,797 | 8 |
| C. albicans | 1,678 | 4 |
| C. glabrata | 1,588 | 11 |
| C. parapsilosis | 1,778 | 44 |
| C. tropicalis | 2,421 | 1 |
| E. coli | 1,607 | 5 |
| G. vaginallis | 1,669 | 5 |
| S. aureus | 1,732 | 8 |
| S. eppidermidis | 1,572 | 2 |
| G. intestinalis | 1,873 | 21 |
| U. urealyticum | 1,813 | 5 |

Example 8

T. vaginalis Pseudo Target for Detuning Amplification

In this example, a pseudo target (SEQ ID NO:61) was evaluated to determine its ability to decrease the sensitivity of the T. vaginalis amplification assay. Pseudo targets have been previously described in Nunomura, U.S. Pat. No. 6,294,338, the contents of which are hereby included by reference herein. Briefly, a pseudo target is an oligonucleotide that is designed to compete with a target for assay resources. The pseudo target binds with a first primer to create a short amplicon that contains a region that will bind with the second primer. The primer binding region of a pseudo target may be altered to increase or decrease its binding affinity and thus increase or decrease the affect of the pseudo target. The short amplicon produced from a pseudo target does not contain a region that would allow a detection probe to bind. Pseudo targets may be created for any amplification oligonucleotide combination. Examples of pseudo targets designed to be used with SEQ ID Nos. 45 and 53 are shown in Table 11 below.

TABLE 11

T. vaginalis Pseudo Targets

| SEQ ID NO. | Sequence |
|---|---|
| 61 | gctaacgagcgagattatcgccaagcaataacaggtccgtgatg |
| 65 | ttgcttggcgataatctcgctcg |
| 66 | cctgttattgcttggcgataatctcgc |
| 67 | cggacctgttattgcttggcgataatctc |

A pseudo target having the nucleotide sequence of SEQ ID NO:61 was evaluated to determine its ability to reduce the sensitivity of an oligonucleotide combination made up of a target capture probe having the nucleotide sequence of SEQ ID NO: 59, amplification oligonucleotides having the nucleotide sequences of SEQ ID Nos. 45 and 53, and Probe T (SEQ ID NO:33 (AE incorporated using a linker positioned between bases 6 and 7). The pseudo target was evaluated using Target Capture, TMA, and HPA. The procedures were the same as those described in Example 3, however the concentrations were as follows. ATCC No. 30001 IVT was diluted to 5e6 copies/mL, 2e5 copies/mL, or 0 copies/mL in Lysis Buffer. The Target Capture Reagent contained 18.5 micrograms (µg) of SEQ ID NO:59. The reconstituted Amplification Reagent contained 53 nanomolar (nM) of SEQ ID NO:45; 53 nM of SEQ ID Nos. 53; and 0, 0.44, 1.3, 4.4, 13, or 44 femtomoles (fmol)/mL of SEQ ID NO:61. Ten replicates were run for each pseudo target concentration at each IVT concentration. The results are summarized in Table 12 below and indicate that the pseudo target concentrations evaluated reduced the sensitivity of the oligonucleotide combination when 2e5 copies/mL of WT were present.

TABLE 12

Pseudo Target Titration Results

| IVT Amt. (copies/mL) | Pseudo Target Amt. (fmol/mL) | Ave. RLU | % CV |
|---|---|---|---|
| 0 | 0 | 100,517 | 74 |
| 0 | 0.44 | 23,539 | 90 |
| 0 | 1.3 | 4,221 | 128 |

TABLE 12-continued

Pseudo Target Titration Results

| IVT Amt. (copies/mL) | Pseudo Target Amt. (fmol/mL) | Ave. RLU | % CV |
|---|---|---|---|
| 0 | 4.4 | 0 | 0 |
| 0 | 13 | 0 | 0 |
| 0 | 44 | 0 | 0 |
| 2e5 | 0 | 1,118,522 | 2 |
| 2e5 | 0.44 | 1,107,886 | 1 |
| 2e5 | 1.3 | 1,052,239 | 2 |
| 2e5 | 4.4 | 713,540 | 3 |
| 2e5 | 13 | 237,831 | 16 |
| 2e5 | 44 | 46,838 | 30 |
| 5e6 | 0 | 1,142,772 | 3 |
| 5e6 | 0.44 | 1,106,056 | 1 |
| 5e6 | 1.3 | 1,123,895 | 8 |
| 5e6 | 4.4 | 1,119,931 | 2 |
| 5e6 | 13 | 1,077,218 | 1 |
| 5e6 | 44 | 775,404 | 11 |

Example 9

Oligonucleotide Combination for Detecting Two Strains of T. vaginalis

In this example, an oligonucleotide combination made up of a target capture probe having the nucleotide sequence of SEQ ID NO: 59, amplification oligonucleotides having the nucleotide sequences of SEQ ID Nos. 45 and 53, a pseudo target having the nucleotide sequence of SEQ ID NO:61, and a Probe T SEQ ID NO:33, AE incorporated using a linker positioned between bases 6 and 7) was evaluated using two T. vaginalis strains, ATCC Nos. 30236 and 50138. Each strain was tested at 0, 0.01, 0.025, 0.05, 0.1, 1, and 5 cells per mL. The T. vaginalis cells were lysed in Lysis Buffer and 400 µL of the lysed cells were transferred to a 12 mm×75 mm tube. The T. vaginalis lysate underwent Target Capture, TMA, and HPA. The procedures and concentrations were the same as those described in Example 3, unless otherwise indicated. The threshold RLU for a positive test was 100,000 RLU. Five replicates were run for each lysate concentration. The results are summarized in Table 13 below and indicate that this oligonucleotide combination was able to detect T. vaginalis cells at a concentration equivalent to 0.1 T. vaginalis cell per mL.

TABLE 13

T. vaginalis Cell Line Testing Results

| | ATCC No. 50138 | | ATCC No. 30236 | |
|---|---|---|---|---|
| Cells/mL | Ave. RLU | % CV | Ave. RLU | % CV |
| 0 | 1,511 | 8 | 1,511 | 8 |
| 0.01 | 18,836 | 24 | 15,840 | 20 |
| 0.025 | 44,968 | 10 | 41,012 | 14 |
| 0.05 | 91,948 | 13 | 85,608 | 8 |
| 0.1 | 164,164 | 11 | 178,063 | 9 |
| 1 | 1,029,097 | 23 | 981,508 | 15 |
| 5 | 1,599,356 | 2 | 1,533,580 | 3 |

Example 10

Oligonucleotide Combination for Detecting T. vaginalis in Clinical Specimens In this example, an oligonucleotide combination made up of a target capture probe having the nucleotide sequence of SEQ ID NO: 59, amplification oligonucleotides having the nucleotide sequences of SEQ ID Nos. 45 and 53, a pseudo target having the nucleotide sequence of SEQ ID NO:61, and Probe T (SEQ ID NO:33, AE incorporated using a linker positioned between bases 6 and 7) was evaluated using two types of clinical specimens spiked with *T. vaginalis* cells. The first type of clinical specimen used was urine samples that were collected from 32 adult females. The urine samples were pooled and diluted 1:1 with Urine Lysis Buffer (ULB). The second type of clinical specimen used was cervical samples collected in ThinPrep® media (Hologic, Inc.; Marlborough, Mass.). The ThinPrep samples were pooled and diluted 1:2.9 with Lysis Buffer (LB). *Trichomonas vaginalis* cells (ATCC No. 30236) were lysed in Lysis Buffer and spiked into the urine-ULB or ThinPrep-LB to a final concentration of 1, 0.3, 0.1, 0.03, 0.01, 0.003, 0.001, and 0 cells per milliliter of urine-ULB or ThinPrep-LB. The spiked clinical specimens underwent Target Capture, TMA and HPA. The procedures and concentrations were the same as those described in Example 3, unless otherwise indicated. Thirty replicates were run for each clinical specimen type at each spike concentration and five replicates were run for each clinical specimen type without spiking. The results are summarized in Table 14 below and indicate that the oligonucleotide combination was able to detect the equivalent of 0.03 *T. vaginalis* cells/mL in either a urine specimen or a ThinPrep specimen.

TABLE 14

Clinical Specimens Results

| Cells/ | Urine | | ThinPrep | |
|---|---|---|---|---|
| mL | Ave. RLU | % CV | Ave. RLU | % CV |
| 0 | 0 | N/A | 0 | N/A |
| 0.001 | 3,414 | 153 | 1,292 | 236 |
| 0.003 | 29,715 | 31 | 12,546 | 61 |
| 0.01 | 120,574 | 15 | 75,762 | 18 |
| 0.03 | 331,695 | 10 | 198,820 | 14 |
| 0.1 | 754,571 | 5 | 527,972 | 6 |
| 0.3 | 1,048,161 | 5 | 874,054 | 6 |
| 1 | 1,096,693 | 5 | 1,016,130 | 5 |

Example 11

Stability of *T. vaginalis* in Cervical Cells Collected in Liquid Based Cytology Media In this example, an oligonucleotide combination made up of a target capture probe having the nucleotide sequence of SEQ ID NO: 59, amplification oligonucleotides having the nucleotide sequences of SEQ ID Nos. 45 and 53, a pseudo target having the nucleotide sequence of SEQ ID NO:61, and Probe T (SEQ ID NO:33, AE incorporated using a linker positioned between bases 6 and 7) was evaluated using cervical cells collected in SurePath® (Becton Dickinson; Franklin Lakes, N.J.) and ThinPrep liquid based cytology media. Cervical samples that were negative for *T. vaginalis* were pooled together and spiked with *T. vaginalis* cells to a final concentration of 1,000 cells per 400 µL of either SurePath or ThinPrep media. The spiked pools were stored at 30° C. Aliquots of 1 mL were removed from the spiked cervical sample pools after 0, 1, and 2 days. The aliquots were added to 2.9 mL of Lysis Buffer. The lysed aliquots were diluted down to 0.1, 1, 10, and 100 cells per 400 µL. Due to the limited nature of the samples, non-spiked samples were not tested.

The SurePath media material safety data sheet lists formaldehyde, which is known to cross-link and degrade nucleic acid. To help reverse the affects of the formaldehyde, some of the aliquots taken from the SurePath sample pool were further treated with FAST Express Reagent (Gen-Probe Cat. No. 102930) before diluting down to 0.1, 1, 10, and 100 cells per 400 µL. For the SurePath sample pool, two aliquots were removed for the day 1 and 2 time points. One of the aliquots was treated with FAST Express Reagent, which consisted of reconstituting the lyophilized reagent with 1 mL of water, adding 100 µL of the reconstituted reagent to the aliquots, and incubating the aliquots at 65° C. for 2 hours.

The diluted samples underwent Target Capture, TMA and HPA. The procedures and concentrations were the same as those described in Example 3, unless otherwise indicated. Ten replicates were run for each dilution level at each time point. The results are summarized in Table 16 below and indicate that the oligonucleotide combination was able to detect the samples collected in ThinPrep media at all dilution levels over the three time points, but was only able detect the specimens collected in SurePath at the 10 or 100 cell dilution level after one day.

TABLE 16

Results for the Liquid Cytology Samples

| | Day 0 | | Day 1 | | Day 2 | |
|---|---|---|---|---|---|---|
| Sample Description | Ave. RLU | % CV | Ave. RLU | % CV | Ave. RLU | % CV |
| SurePath 100 cells | 1,227,100 | 2 | 1,193,900 | 3.66 | 1,171,000 | 3.88 |
| SurePath 10 cells | 1,226,300 | 3 | 604,000 | 16.95 | 298,100 | 6.40 |
| SurePath 1 cell | 1,178,200 | 5 | 52,900 | 24.17 | 34,000 | 20.84 |
| Surepath 0.1 cell | 468,000 | 8 | 6,900 | 62.78 | 4,900 | 32.55 |
| SurePath 100 cells + Fast Express | NT | NT | 1,016,400 | 2.26 | 992,100 | 3.85 |
| SurePath 10 cells + Fast Express | NT | NT | 248,800 | 5.91 | 227,900 | 9.00 |
| SurePath 1 cell + Fast Express | NT | NT | 27,000 | 15.91 | 27,100 | 13.30 |
| Surepath 0.1 cell + Fast Express | NT | NT | 6,000 | 38.49 | 5,400 | 30.49 |
| ThinPrep 100 cells | 1,219,400 | 3 | 1,254,000 | 4.99 | 1,254,800 | 4.17 |
| ThinPrep 10 cells | 1,250,800 | 2 | 1,239,200 | 4.29 | 1,206,200 | 3.11 |
| ThinPrep 1 cell | 1,209,600 | 2 | 958,000 | 2.90 | 859,300 | 4.62 |
| ThinPrep 0.1 cell | 754,300 | 2 | 209,900 | 8.62 | 166,200 | 10.14 |

"NT" means not tested

Example 12

New Target Capture Probes for Detecting *T. vaginalis* in Samples Collected in SurePath Media In this example, several new target capture probes (SEQ ID NO:89, SEQ ID NO:94, SEQ ID NO:99, SEQ ID NO:104, SEQ ID NO:105, and SEQ ID NO:106) were evaluated in two different experiments. The performance of SEQ ID NO:59 in samples collected in SurePath media prompted the development of new target capture probes that would perform better with samples collected in SurePath media. The new target capture probes were compared to SEQ ID NO:59.

In the first experiment, SEQ ID NO:89 (first 22 bases were 2'-O-Methyl RNA), SEQ ID NO:94, SEQ ID NO:105 (first 24 bases were 2'-O-Methyl RNA), and SEQ ID NO:106 (first 19 bases were 2'-O-Methyl RNA) were evaluated against SEQ ID NO:59. *Trichomonas vaginalis* cells were tested at 0.2 cells per mL of Lysis Buffer. The new target capture probes were tested at 0.5 and 1 pmol per 100 µL of Target Capture Reagent. SEQ ID NO:89, SEQ ID NO:105, and SEQ ID NO:106 were evaluated as 2'-O-Methyl RNA oligonucleotides, whereas SEQ ID NO:94 and SEQ ID NO:59 were evaluated as DNA oligonucleotides. The target capture probes were evaluated using amplification oligonucleotides having the nucleotide sequences of SEQ ID Nos. 45 and 53, a pseudo target having the nucleotide sequence of SEQ ID NO:61, and Probe T (SEQ ID NO:33, AE incorporated using a linker positioned between bases 6 and 7). The samples underwent Target Capture, TMA and HPA. The procedures and concentrations were the same as those described in Example 3, unless otherwise indicated. Twenty replicates were run thr each target capture probe. The results are summarized in Table 17 below and indicate that SEQ ID NO:94, SEQ ID NO:105, and SEQ ID NO:106 perform similar to or better than SEQ ID NO:59.

TABLE 17

Results for the New Target Capture Probes, First Experiment

| Target Capture Probe and Amount | 0.2 cells/ml | |
|---|---|---|
| | Ave. RLU | % CV |
| SEQ ID NO: 59 | 296,572 | 25 |
| SEQ ID NO: 89 at 1 | 86,273 | 12 |
| SEQ ID NO: 94 at 1 | 304,351 | 9 |
| SEQ ID NO: 105 at 1 | 893,675 | 8 |
| SEQ ID NO: 106 at 1 | 810,486 | 8 |
| SEQ ID NO: 89 at 0.5 | 141,617 | 15 |
| SEQ ID NO: 94 at 0.5 | 224,187 | 10 |
| SEQ ID NO: 105 at 0.5 | 732,092 | 15 |
| SEQ ID NO: 106 at 0.5 | 645,401 | 6 |

In the second experiment, SEQ ID NO:99 and SEQ ID NO:104 were evaluated against SEQ ID NO:59. The new target capture probes were evaluated at 1 pmol per 100 µL of Target Capture Reagent. *Trichomonas vaginalis* in vitro transcript was tested at 0, 2e5 and 1e6 copies per mL of Lysis Buffer and *T. vaginalis* cells were tested at 0 and 13 cells per mL of Lysis Buffer. The target capture probes were evaluated using amplification oligonucleotides having the nucleotide sequences of SEQ ID Nos. 45 and 53, a pseudo target having the nucleotide sequence of SEQ ID NO:61, and a Probe T (SEQ ID NO:33, AE incorporated using a linker positioned between bases 6 and 7). The samples underwent Target Capture, TMA and HPA. The procedures and concentrations were the same as those described in Example 3, unless otherwise indicated. Eight replicates were run samples containing 0 or 2e5 copies of in vitro transcript and 12 replicates were run for samples containing 1e6 copies of in vitro transcript. Two replicates were run for the samples containing cells. The results are summarized in Table 18 below and indicate that SEQ ID NO:99 and SEQ ID NO:104 perform poorer than SEQ ID NO:59 at low levels of detection.

TABLE 18

Results for the New Target Capture Probes, Second Experiment

| Target Capture Probe, Sample | Ave RLU | % CV |
|---|---|---|
| SEQ ID NO: 59, 0 cells | 2,500 | 85 |
| SEQ ID NO: 59, 13 cells | 1,244,000 | 3 |
| SEQ ID NO: 59, 0 IVT | 2,625 | 40 |
| SEQ ID NO: 59, 2e5 IVT | 1,008,125 | 6 |
| SEQ ID NO: 59, 1e6 IVT | 393,333 | 9 |
| SEQ ID NO: 99, 0 cells | 2,000 | 0 |
| SEQ ID NO: 99, 13 cells | 876,500 | 13 |
| SEQ ID NO: 99, 0 IVT | 3,250 | 32 |
| SEQ ID NO: 99, 2e5 IVT | 11,625 | 32 |
| SEQ ID NO: 99, 1e6 IVT | 4,833 | 36 |
| SEQ ID NO: 104, 0 cells | 3,500 | 61 |
| SEQ ID NO: 104, 13 cells | 130,108 | 13 |
| SEQ ID NO: 104, 0 IVT | 3,125 | 63 |
| SEQ ID NO: 104, 2e5 IVT | 23,250 | 29 |
| SEQ ID NO: 104, 1e6 IVT | 6,917 | 37 |

Example 13

Dual-Target Capture Probes for Detecting *T. vaginalis* in Cervical Cells Collected in SurePath Media In this example, an oligonucleotide combination made up of two target capture probes having nucleotide sequences of SEQ ID NO: 59 (at 0.1 pmol/100 µL) and SEQ ID NO:94 (at 1.5 pmol/100 µL), amplification oligonucleotides having the nucleotide sequences of SEQ ID Nos. 45 and 53, a pseudo target having the nucleotide sequence of SEQ ID NO:61, and Probe T (SEQ ID NO:33, AE incorporated using a linker positioned between bases 6 and 7) was evaluated using cervical cells collected in SurePath liquid based cytology media. Cervical samples that were negative for *T. vaginalis* were spiked with *T. vaginalis* cells to a final concentration of 1,000 cells per 400 µL of SurePath media. Aliquots of 500 µL were removed from the spiked cervical samples at 0 and 3 days and added to 2.9 mL of Lysis Buffer. The lysed samples were treated with 100 µL of FAST Express Reagent that was reconstituted in 1 mL of water. The samples were incubated at 65° C. for 2 hours. Following the incubation, the samples were diluted to 1, 10, and 100 cells per 400 µL. The diluted samples underwent Target Capture, TMA and HPA. The procedures and concentrations were the same as those described in Example 3, unless otherwise indicated. The day 3 samples were also tested using the oligonucleotide combination described in Example 11 (SEQ ID Nos. 45, 53, 59, 61, and Probe T). Four replicates were run for each clinical specimen at the three dilution levels for the day 0. Three replicates were run for all others. The results are summarized in Table 19 below and indicate that the dual-target capture oligonucleotide combination performed better than single target capture oligonucleotide combination at detecting 1 cell per 400 µL.

TABLE 19

Results for Single and Dual Target Capture Probes

| Sample ID & Description | Single Target Capture Probe Day 3 | | Dual Target Capture Probes Day 0 | | Dual Target Capture Probes Day 3 | |
|---|---|---|---|---|---|---|
| | Ave RLU | % CV | Ave RLU | % CV | Ave RLU | % CV |
| 1 at 100 cells | 1,174,667 | 1 | 1,385,000 | 3 | 1,435,333 | 0 |
| 1 at 10 cells | 219,000 | 7 | 1,270,750 | 2 | 1,079,333 | 4 |
| 1 at 1 cell | 26,667 | 16 | 1,250,000 | 2 | 217,667 | 9 |
| 1 at 0 cells | NT | NT | 1,333 | 43 | NT | NT |
| 2 at 100 cells | 1,313,333 | 6 | 1,372,667 | 1 | 1,443,333 | 1 |
| 2 at 10 cells | 1,262,000 | 2 | 1,277,000 | 2 | 1,421,667 | 4 |
| 2 at 1 cell | 380,000 | 6 | 1,267,500 | 0 | 1,409,333 | 2 |
| 2 at 0 cells | NT | NT | 1,333 | 43 | NT | NT |
| 3 at 100 cells | 1,399,000 | 2 | 1,407,500 | 3 | 1,428,333 | 2 |
| 3 at 10 cells | 889,000 | 5 | 1,269,000 | 2 | 1,445,000 | 2 |
| 3 at 1 cell | 1,667 | 35 | 1,265,250 | 2 | 1,667 | 35 |
| 3 at 0 cells | NT | NT | 1,667 | 69 | NT | NT |
| 6 at 100 cells | 1,387,667 | 1 | 1,377,000 | 4 | 1,468,667 | 1 |
| 6 at 10 cells | 1,019,667 | 3 | 1,288,000 | 2 | 1,450,000 | 3 |
| 6 at 1 cell | 22,333 | 9 | 1,252,250 | 2 | 1,409,000 | 2 |
| 6 at 0 cells | NT | NT | 2,667 | 43 | NT | NT |
| 8 at 100 cells | 995,000 | 1 | 1,418,667 | 2 | 1,409,667 | 2 |
| 8 at 10 cells | 183,000 | 15 | 1,296,000 | 1 | 1,246,333 | 1 |
| 8 at 1 cell | 22,333 | 9 | 1,274,500 | 1 | 330,667 | 8 |
| 8 at 0 cells | NT | NT | 1,000 | 0 | NT | NT |
| 9 at 100 cells | 1,152,667 | 0 | 1,394,667 | 2 | 1,441,000 | 2 |
| 9 at 10 cells | 221,333 | 7 | 1,275,750 | 3 | 1,339,667 | 2 |
| 9 at 1 cell | 29,000 | 27 | 1,256,750 | 3 | 486,000 | 6 |
| 9 at 0 cells | NT | NT | 1,667 | 35 | NT | NT |
| 10 at 100 cells | 1,334,667 | 2 | 1,357,333 | 1 | 1,433,667 | 2 |
| 10 at 10 cells | 486,000 | 11 | 1,272,750 | 1 | 1,161,667 | 1 |
| 10 at 1 cell | 2,000 | 0 | 1,262,000 | 2 | 383,000 | 2 |
| 10 at 0 cells | NT | NT | 1,333 | 43 | NT | NT |
| 13 at 100 cells | 1,124,333 | 8 | 1,369,667 | 2 | 1,365,000 | 4 |
| 13 at 10 cells | 219,000 | 10 | 1,266,000 | 1 | 972,000 | 2 |
| 13 at 1 cell | 20,667 | 7 | 1,252,500 | 3 | 164,000 | 9 |
| 13 at 0 cells | NT | NT | 6,333 | 40 | NT | NT |

"NT" means not tested

While the disclosure has been described and shown in considerable detail with reference to certain embodiments, those skilled in the art will readily appreciate other embodiments of the disclosure. Accordingly, the disclosure is deemed to include all modifications and variations encompassed within the spirit and scope of the following appended claims.

The invention claimed is:

1. A probe for use in determining the presence of *Trichomonas vaginalis* in a sample, the probe consisting of an oligonucleotide and one or more labels, each of the labels being joined to the oligonucleotide with a non-nucleotide linker, wherein the oligonucleotide consists of a target-complementary sequence and, optionally, one or more flanking sequences which, under stringent hybridization conditions, do not stably bind to a target nucleic acid derived from *Trichomonas vaginalis* when the target-complementary sequence is stably hybridized to the target nucleic acid, and wherein the base sequence of the target-complementary sequence consists of the base sequence of SEQ ID NO:33, SEQ ID NO:34, SEQ ID NO:35 or SEQ ID NO:36, or an RNA/DNA combination equivalent of any of the foregoing.

2. The probe of claim 1, wherein the probe includes one or more of the flanking sequences.

3. The probe of claim 2, wherein the probe includes two of the flanking sequences directly joined to opposite ends of the target-complementary sequence.

4. The probe of claim 3, wherein the two flanking sequences are complementary to each other.

5. The probe of claim 2, wherein the probe includes two of the flanking sequences joined to opposite ends of the target-complementary sequence, each of the two flanking sequences being directly joined to the target-complementary sequence or joined to the target-complementary sequence by means of a non-nucleotide linker.

6. The probe of claim 5, wherein the two flanking sequences are complementary to each other.

7. The probe of claim 1, wherein the probe does not include the flanking sequences.

8. The probe of claim 1, wherein the target-complementary sequence is an RNA or DNA analog or contains one or more modified nucleosides.

9. The probe of claim 8, wherein the base sequence of the target-complementary sequence consists of the base sequence of SEQ ID NO:34 or SEQ ID NO:36, and wherein each of the ribonucleosides of the target-complementary sequence has a 2'-O-methyl substitution to the ribofuranosyl moiety.

10. The probe of claim 8, wherein the base sequence of the target-complementary sequence consists of the base sequence of SEQ ID NO:33 or SEQ ID NO:35, and wherein the target-complementary sequence is a peptide nucleic acid.

11. The probe of claim 1, wherein the one or more labels are non-isotopic.

12. The probe of claim 11, wherein the one or more labels include at least one of a chemiluminescent molecule and a fluorescent molecule.

13. The probe of claim 11, wherein the one or more labels include a pair of interacting labels.

14. The probe of claim 13, wherein the probe includes two of the flanking sequences joined to opposite ends of the target-complementary sequence, and wherein the flanking sequences are complementary to each other.

15. The probe of claim 14, wherein the probe is a molecular beacon probe or a molecular torch probe.

16. The probe of claim 1, wherein the stringent hybridization conditions include a temperature of about 60° C. and a salt concentration of about 1.5M.

17. A method for determining the presence of *Trichomonas vaginalis* in a sample, the method comprising the steps of:

(a) contacting a sample with the probe of claim 1 under conditions permitting the probe to preferentially hybridize to nucleic acid derived from *Trichomonas vaginalis* and not to nucleic acid derived from *Trichomonas tenax*; and (b) determining whether a hybrid comprising the probe hybridized to the *Trichomonas vaginalis*-derived nucleic acid has formed as indication of the presence of *Trichomonas vaginalis* in the sample.

18. The method of claim 17, wherein the probe includes two of the flanking sequences joined to opposite ends of the target-complementary sequence, each of the two flanking sequences being directly joined to the target-complementary sequence or joined to the target-complementary sequence by means of a non-nucleotide linker.

19. The method of claim 18, wherein the two flanking sequences are complementary to each other.

20. The method of claim 17, wherein the probe does not include the flanking sequences.

* * * * *